(12) United States Patent
Ramsay et al.

(10) Patent No.: US 11,026,730 B2
(45) Date of Patent: Jun. 8, 2021

(54) BONE ANCHORS WITH DRAG FEATURES AND RELATED METHODS

(71) Applicant: Medos International Sarl, Le Locle (CH)

(72) Inventors: Christopher Ramsay, West Wareham, MA (US); J. Riley Hawkins, Cumberland, RI (US); Albert Montello, Duxbury, MA (US); Joseph Peterson, South Dartmouth, MA (US)

(73) Assignee: Medos International Sarl, Le Locle (CH)

( * ) Notice: Subject to any disclaimer, the term of this patent is extended or adjusted under 35 U.S.C. 154(b) by 297 days.

(21) Appl. No.: 15/591,608

(22) Filed: May 10, 2017

(65) Prior Publication Data

US 2018/0325569 A1 Nov. 15, 2018

(51) Int. Cl.
*A61B 17/70* (2006.01)
*A61B 17/86* (2006.01)

(52) U.S. Cl.
CPC ...... *A61B 17/8605* (2013.01); *A61B 17/7032* (2013.01); *A61B 17/7037* (2013.01); *A61B 17/8685* (2013.01)

(58) Field of Classification Search
CPC .. A61B 17/7034–7035; A61B 17/7037; A61B 17/7032; A61B 17/8605
USPC .................. 606/300–321, 246–279
See application file for complete search history.

(56) References Cited

U.S. PATENT DOCUMENTS

| | | |
|---|---|---|
| 4,946,458 A | 8/1990 | Harms et al. |
| 5,443,467 A | 8/1995 | Biedermann et al. |
| 5,536,268 A | 7/1996 | Griss |
| 5,672,176 A | 9/1997 | Biedermann et al. |
| 5,733,285 A | 3/1998 | Errico et al. |

(Continued)

FOREIGN PATENT DOCUMENTS

| | | |
|---|---|---|
| CN | 103565504 A | 2/2014 |
| DE | 10005386 A1 | 8/2001 |

(Continued)

OTHER PUBLICATIONS

[NoAuthorListed] Expedium Verse® Spinal System, System Guide, 2015, 52 pages.

(Continued)

*Primary Examiner* — Jessica Weiss
(74) *Attorney, Agent, or Firm* — Nutter McClennen & Fish LLP

(57) ABSTRACT

Bone anchors and related methods are disclosed herein. In some embodiments, a bone anchor can include a drag interface. Exemplary drag interfaces include (i) friction between a shank and a bushing, (ii) friction between a bushing and a drag ring, (iii) friction generated by a biased saddle, and (iv) combinations of the above. The drag interface can help maintain the relative position between a receiver member and a shank of the bone anchor prior to locking the bone anchor, preventing unintended movement while still allowing free movement when intended by the user. In some embodiments, a bone anchor can include over-rotation blocking features, such as a groove, lip, or protrusion formed on a bushing of the bone anchor. Various other bone anchor features are also disclosed, including high aspect ratio drag rings and compressible drag posts.

21 Claims, 16 Drawing Sheets

(56) References Cited

U.S. PATENT DOCUMENTS

| | | | |
|---|---|---|---|
| 5,733,286 A | 3/1998 | Errico et al. | |
| 5,782,833 A | 7/1998 | Haider | |
| 5,879,350 A | 3/1999 | Sherman et al. | |
| 5,885,286 A | 3/1999 | Sherman et al. | |
| 5,891,145 A | 4/1999 | Morrison et al. | |
| 5,961,517 A | 10/1999 | Biedermann et al. | |
| 6,063,090 A | 5/2000 | Schlapfer | |
| 6,090,111 A | 7/2000 | Nichols | |
| 6,113,601 A | 9/2000 | Tatar | |
| 6,248,105 B1 | 6/2001 | Schlapfer et al. | |
| 6,254,602 B1 | 7/2001 | Justis | |
| 6,280,442 B1 | 8/2001 | Barker et al. | |
| 6,287,311 B1 | 9/2001 | Sherman et al. | |
| 6,355,040 B1 | 3/2002 | Richelsoph et al. | |
| 6,371,957 B1 | 4/2002 | Amrein et al. | |
| 6,402,752 B2 | 6/2002 | Schaffler-Wachter et al. | |
| 6,471,705 B1 | 10/2002 | Biedermann et al. | |
| 6,485,491 B1 | 11/2002 | Farris et al. | |
| 6,540,748 B2 | 4/2003 | Lombardo | |
| 6,582,436 B2 | 6/2003 | Schlapfer et al. | |
| 6,585,737 B1 | 7/2003 | Baccelli et al. | |
| 6,660,004 B2 | 12/2003 | Barker et al. | |
| 6,736,820 B2 | 5/2004 | Biedermann et al. | |
| 6,835,196 B2 | 12/2004 | Biedermann et al. | |
| 6,837,889 B2 | 1/2005 | Shluzas | |
| 6,869,433 B2 | 3/2005 | Glascott | |
| 6,974,460 B2 | 12/2005 | Carbone et al. | |
| 7,066,937 B2 | 6/2006 | Shluzas | |
| 7,081,116 B1 | 7/2006 | Carly | |
| 7,087,057 B2 | 8/2006 | Konieczynski et al. | |
| 7,144,396 B2 | 12/2006 | Shluzas | |
| 7,179,261 B2 | 2/2007 | Sicvol et al. | |
| 7,316,684 B1 | 1/2008 | Baccelli et al. | |
| 7,604,656 B2 | 10/2009 | Shluzas | |
| 7,682,377 B2 | 3/2010 | Konieczynski et al. | |
| 7,699,876 B2 * | 4/2010 | Barry | A61B 17/7037 606/266 |
| 7,727,261 B2 | 6/2010 | Barker et al. | |
| 7,879,075 B2 | 2/2011 | Shluzas | |
| 7,942,910 B2 | 5/2011 | Doubler et al. | |
| 7,951,173 B2 | 5/2011 | Hammill, Sr. et al. | |
| 8,021,397 B2 * | 9/2011 | Farris | A61B 17/7037 606/266 |
| 8,062,339 B2 | 11/2011 | Hammer et al. | |
| 8,133,262 B2 | 3/2012 | Whipple | |
| 8,197,517 B1 | 6/2012 | Lab et al. | |
| 8,298,274 B2 | 10/2012 | Barker, Jr. et al. | |
| 8,313,516 B2 | 11/2012 | Konieczynski et al. | |
| 8,337,530 B2 | 12/2012 | Hestad et al. | |
| 8,444,681 B2 | 5/2013 | Jackson et al. | |
| 8,529,604 B2 | 9/2013 | Barker, Jr. et al. | |
| 8,556,938 B2 | 10/2013 | Jackson et al. | |
| 8,663,288 B2 | 3/2014 | Konieczynski et al. | |
| 8,663,290 B2 | 3/2014 | Doubler et al. | |
| 8,709,050 B2 | 4/2014 | Shluzas | |
| 8,709,051 B2 | 4/2014 | Hammer et al. | |
| 8,906,068 B1 | 12/2014 | Bedor | |
| 8,936,624 B2 | 1/2015 | Shluzas | |
| 8,951,290 B2 | 2/2015 | Hammer et al. | |
| 8,998,959 B2 | 4/2015 | Jackson et al. | |
| 9,023,086 B2 | 5/2015 | Biedermann et al. | |
| 9,149,300 B2 | 10/2015 | Biedermann et al. | |
| 9,168,069 B2 | 10/2015 | Jackson et al. | |
| 9,186,191 B2 | 11/2015 | Berrevoets et al. | |
| 9,232,969 B2 | 1/2016 | Farris | |
| 9,241,737 B2 | 1/2016 | Biedermann et al. | |
| 9,271,761 B2 | 3/2016 | Legallois et al. | |
| 9,603,632 B1 | 3/2017 | Gunn et al. | |
| 9,655,657 B2 | 5/2017 | Konieczynski et al. | |
| 9,763,700 B1 * | 9/2017 | Gregory | A61B 17/7037 606/266 |
| 2007/0118123 A1 * | 5/2007 | Strausbaugh | A61B 17/7032 606/272 |
| 2008/0015597 A1 | 1/2008 | Whipple | |
| 2008/0249570 A1 * | 10/2008 | Carson | A61B 17/7038 606/264 |
| 2008/0262556 A1 * | 10/2008 | Jacofsky | A61B 17/7076 606/308 |
| 2010/0114174 A1 | 5/2010 | Jones et al. | |
| 2011/0040338 A1 * | 2/2011 | Jackson | A61B 17/7032 606/305 |
| 2011/0087288 A1 | 4/2011 | Stevenson et al. | |
| 2011/0098755 A1 * | 4/2011 | Jackson | A61B 17/8605 606/305 |
| 2011/0288599 A1 | 11/2011 | Michielli et al. | |
| 2012/0089150 A1 | 4/2012 | Smith | |
| 2012/0136395 A1 * | 5/2012 | Biedermann | A61B 17/7037 606/279 |
| 2012/0143265 A1 | 6/2012 | Biedermann et al. | |
| 2012/0165881 A1 | 6/2012 | Biedermann et al. | |
| 2012/0253408 A1 | 10/2012 | Timm | |
| 2012/0303072 A1 | 11/2012 | Eisermann | |
| 2012/0310284 A1 | 12/2012 | Gerchow | |
| 2013/0053901 A1 | 2/2013 | Cormier et al. | |
| 2013/0066376 A1 | 3/2013 | Biedermann et al. | |
| 2013/0096620 A1 | 4/2013 | Biedermann et al. | |
| 2013/0165977 A1 | 6/2013 | Biedermann et al. | |
| 2013/0197586 A1 | 8/2013 | Matthis et al. | |
| 2013/0218213 A1 * | 8/2013 | Lemoine | A61B 17/7032 606/305 |
| 2013/0338716 A1 | 12/2013 | Biedermann et al. | |
| 2014/0012337 A1 | 1/2014 | Biedermann et al. | |
| 2014/0094849 A1 * | 4/2014 | Spratt | A61B 17/7037 606/257 |
| 2014/0121703 A1 | 5/2014 | Jackson et al. | |
| 2014/0142634 A1 * | 5/2014 | Schlaepfer | A61B 17/704 606/278 |
| 2014/0163618 A1 | 6/2014 | Legallois et al. | |
| 2014/0188173 A1 | 7/2014 | Mishra et al. | |
| 2014/0277161 A1 * | 9/2014 | Spratt | A61B 17/8685 606/278 |
| 2014/0343617 A1 | 11/2014 | Hannen | |
| 2014/0358182 A1 | 12/2014 | Puekert | |
| 2015/0032162 A1 | 1/2015 | Biedermann et al. | |
| 2015/0173816 A1 * | 6/2015 | Biedermann | A61B 17/7037 606/308 |
| 2015/0282844 A1 | 10/2015 | Vedula et al. | |
| 2016/0000470 A1 | 1/2016 | Matthis et al. | |
| 2016/0030086 A1 | 2/2016 | Mishra | |
| 2016/0038204 A1 | 2/2016 | Biedermann et al. | |
| 2016/0045228 A1 | 2/2016 | Biedermann et al. | |
| 2016/0183982 A1 * | 6/2016 | Bazille | A61B 17/7035 606/266 |
| 2016/0192966 A1 | 7/2016 | Biedermann et al. | |
| 2016/0317206 A1 * | 11/2016 | Rezach | A61B 17/7037 606/308 |
| 2017/0209185 A1 | 7/2017 | Trautwein et al. | |

FOREIGN PATENT DOCUMENTS

| | | |
|---|---|---|
| EP | 1 210 914 A1 | 6/2002 |
| EP | 2 687 171 A1 | 1/2014 |
| EP | 2 687 172 A1 | 1/2014 |
| EP | 2 687 171 B1 | 4/2015 |
| WO | 2000/076413 A1 | 12/2000 |
| WO | 01/006940 A1 | 2/2001 |
| WO | 01/10317 A1 | 2/2001 |
| WO | 03/037199 A1 | 5/2003 |
| WO | 2013/063477 A1 | 5/2013 |
| WO | 2016/020158 A1 | 2/2016 |

OTHER PUBLICATIONS

[NoAuthorListed] Synapse System Technique Guide, Synthes Spine, 2007, 51 pages.

[NoAuthorListed] Synapse System Surgical Technique, DePuy Synthes, 2016, 68 pages.

(56) References Cited

OTHER PUBLICATIONS

International Search Report and Written Opinion for Application No. PCT/US2018/031296, dated Oct. 10, 2018 (20 Pages).

\* cited by examiner

FIG. 2B
FIG. 2C
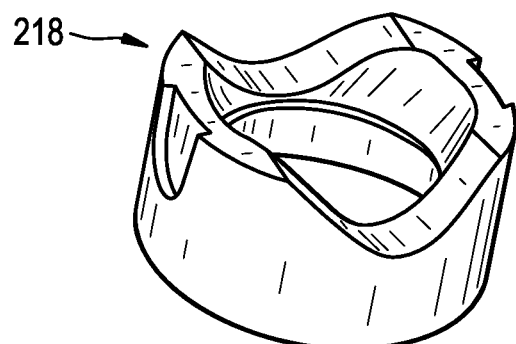
FIG. 2D
FIG. 2E
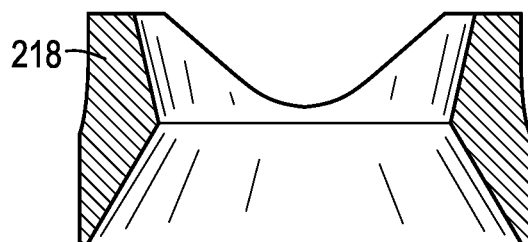
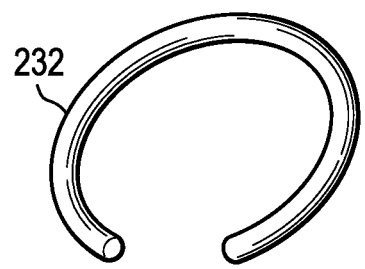
FIG. 2F
FIG. 2G
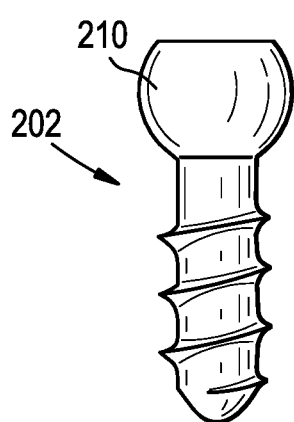
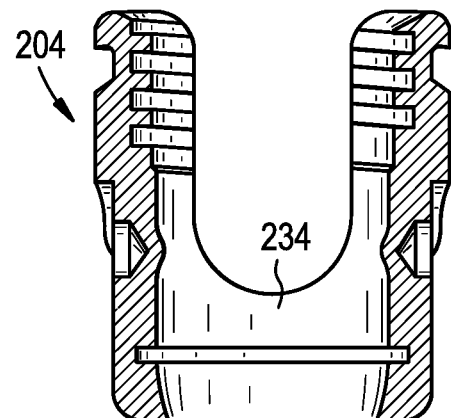

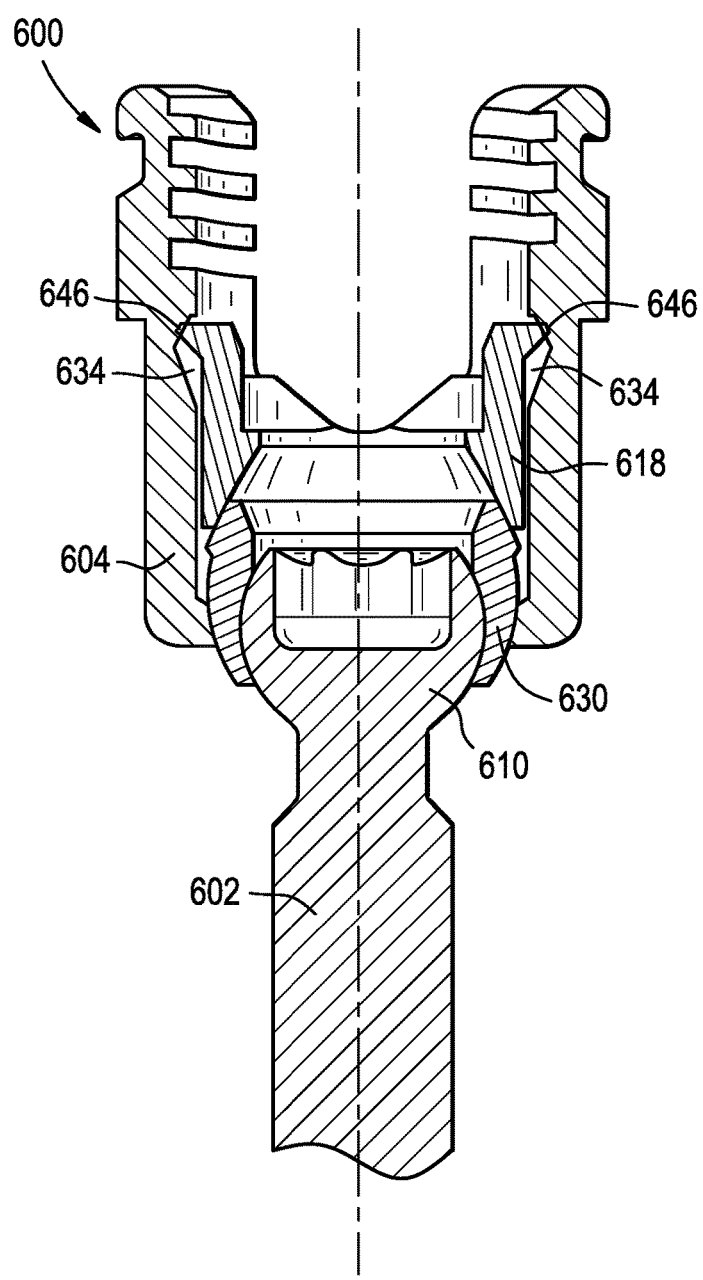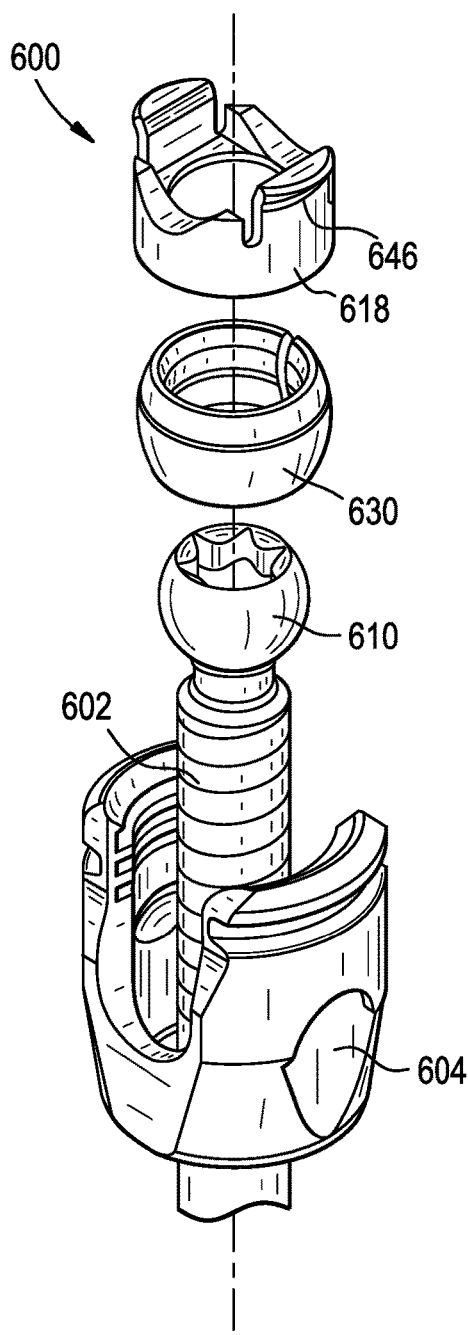

BONE ANCHORS WITH DRAG FEATURES AND RELATED METHODS

FIELD

Bone anchors with drag features and related methods are disclosed herein.

BACKGROUND

Bone anchors can be used in orthopedic surgery or neurosurgery to fix bone during healing, fusion, or other processes. In spinal surgery, for example, bone anchors can be used to secure a spinal fixation element, such as a rod or plate, to one or more vertebrae to rigidly or dynamically stabilize the spine.

A typical bone anchor can include a threaded shank portion configured to be anchored in bone and a head or receiver member attached to the shank portion and configured to receive a rod or other element therein. A number of bone anchors have been developed in which the receiver member is, at least initially, movably-coupled to the shank portion. While this freedom of movement can be helpful when aligning multiple components of a fixation assembly, it can also introduce challenges for the user. For example, it can be difficult to maintain a desired angular orientation between the receiver member and the shank prior to locking the construct. Thus, during provisional positioning of the implanted construct, the receiver members can have a tendency to "flop" over, requiring subsequent repositioning by the user to achieve the desired alignment, or requiring the user or an assistant to hold the receiver member in the desired position during rod introduction. This can be cumbersome for the user, potentially leading to fatigue and adding unnecessary length to the surgery.

In view of these and other challenges, there is a continual need for improved bone anchors and related methods.

SUMMARY

Bone anchors and related methods are disclosed herein. In some embodiments, a bone anchor can include a drag interface. Exemplary drag interfaces include (i) friction between a shank and a bushing, (ii) friction between a bushing and a drag ring, (iii) friction generated by a biased saddle, and (iv) combinations of the above. The drag interface can help maintain the relative position between a receiver member and a shank of the bone anchor prior to locking the bone anchor, preventing unintended movement while still allowing free movement when intended by the user. In some embodiments, a bone anchor can include over-rotation blocking features, such as a groove, lip, or protrusion formed on a bushing of the bone anchor. Various other bone anchor features are also disclosed, including high aspect ratio drag rings and compressible drag posts.

In some embodiments, a bone anchor can include a receiver member that defines a cavity and a rod-receiving recess, the receiver member having proximal and distal ends and a central longitudinal axis; a bushing disposed in the cavity; a shank having a head portion retained within the bushing and a bone engaging portion that protrudes distally from the receiver member; and a drag ring that applies a frictional force to the bushing, the drag ring being disposed in a groove formed in the receiver member.

The head portion of the shank can be rotatable with respect to the bushing. The bushing can exert a frictional force on the head of the shank. The bone anchor can include a fastener configured to be applied to the receiver member to (i) prevent rotation of the head portion of the shank relative to the bushing and (ii) prevent rotation of the bushing relative to the receiver member. The bushing can include an over-rotation blocking feature. The blocking feature can include a lip formed at a proximal end of the bushing, the lip being configured to contact the drag ring to limit rotation of the bushing relative to the receiver member. The drag ring can have a ramped distal-facing surface oriented at an oblique angle to the central longitudinal axis of the receiver member. The drag ring can have a planar proximal-facing surface oriented perpendicular to the central longitudinal axis of the receiver member. The blocking feature can include a lip formed at a proximal end of the bushing, the lip being configured to contact the groove of the receiver member to limit rotation of the bushing relative to the receiver member. The blocking feature can include a lip formed at a proximal end of the bushing, the lip being configured to contact a distal seat of the receiver member to limit rotation of the bushing relative to the receiver member. The bone anchor can include a saddle disposed in the cavity proximal to the bushing, wherein the saddle includes a distal-facing surface with a drag pin extending distally therefrom.

In some embodiments, a bone anchor can include a receiver member that defines a cavity and a rod-receiving recess, the receiver member having proximal and distal ends and a central longitudinal axis; a saddle disposed in the cavity; and a shank having a head portion disposed in the cavity distal to the saddle and a bone engaging portion that protrudes distally from the receiver member. The saddle can be biased distally to exert a drag force on the shank.

The shank can include a bushing in which the head portion is disposed. The saddle can exert the drag force on the bushing. The bone anchor can include a ring disposed partially in a first groove formed in the saddle and partially in a second groove formed in the receiver member, the ring being biased against a ramped surface of one of the first and second grooves to urge the saddle distally relative to the receiver member. The saddle can include first and second arms that define a rod-receiving recess therebetween. The first and second arms can include protrusions received within corresponding recesses of the receiver member to limit rotation of the saddle relative to the receiver member about the central longitudinal axis of the receiver member. The first and second arms can include ears that are biased against a ramped surface of the receiver member to urge the saddle distally relative to the receiver member. The ears can be biased by resilient material properties of the arms. The ears can be biased by radial expansion of the saddle. The saddle can include a split to facilitate said radial expansion. The saddle can be longitudinally-expandable to urge the saddle distally relative to the receiver member. The saddle can include proximal and distal portions and a bias element configured to urge the proximal and distal portions away from one another to longitudinally-expand the saddle. The bias element can include a wave spring. The receiver member can include a proximal shoulder in contact with the proximal portion of the saddle such that the bias element urges the distal portion of the saddle distally relative to the receiver member. The saddle can include a distal-facing surface with a drag pin extending distally therefrom.

In some embodiments, a bone anchor can include a receiver member that defines a cavity and a rod-receiving recess, the receiver member having proximal and distal ends and a central longitudinal axis; a bushing disposed in the cavity, the bushing being polyaxially rotatable within the cavity, the bushing having an exterior lip configured to contact a component of the bone anchor to limit said polyaxial rotation; and a shank having a head portion retained within the bushing and a bone engaging portion that protrudes distally from the receiver member, the head portion of the shank being polyaxially rotatable relative to the bushing.

The component of the bone anchor can include a ring received within a groove formed in the receiver member. The ring can have a ramped distal-facing surface oriented at an oblique angle to the central longitudinal axis of the receiver member. The ring can have a planar proximal-facing surface oriented perpendicular to the central longitudinal axis of the receiver member. The component of the bone anchor can include a floor of a groove formed in the receiver member. The component of the bone anchor can include a distal seat of the receiver member.

In some embodiments, a bone anchor can include a receiver member that defines a cavity and a rod-receiving recess, the receiver member having proximal and distal ends and a central longitudinal axis; a shank having a head portion disposed in the cavity and a bone engaging portion that protrudes distally from the receiver member; and a drag ring that applies a frictional force to the shank to resist rotation of the shank relative to the receiver member. The drag ring can have a height dimension parallel to the central longitudinal axis of the receiver member, the height dimension extending from a proximal surface of the drag ring to a distal surface of the drag ring. The drag ring can have a width dimension perpendicular to the height dimension, the width dimension extending from an inner surface of the drag ring to an outer surface of the drag ring. A ratio of the height dimension to the width dimension can be at least 2:1. The ratio of the height dimension to the width dimension can be at least 4:1.

In some embodiments, a surgical method can include driving a shank portion of a bone anchor into a bone of a patient; positioning a receiver member of the bone anchor at a desired position relative to the shank portion; tightening a fastener of the bone anchor to lock movement between the receiver member and the shank; and before tightening the fastener, retaining the receiver member in the desired position by a drag force exerted by a drag ring against a bushing in which a head of the shank portion is disposed.

Retaining the receiver member can include retaining the receiver member by a drag force exerted by the bushing against the head of the shank portion.

In some embodiments, a surgical method can include driving a shank portion of a bone anchor into a bone of a patient; positioning a receiver member of the bone anchor at a desired position relative to the shank portion; tightening a fastener of the bone anchor to lock movement between the receiver member and the shank; and before tightening the fastener, retaining the receiver member in the desired position by a drag force exerted by a biased saddle of the bone anchor.

Retaining the receiver member can include retaining the receiver member by a drag force exerted by a bushing of the bone anchor against a head of the shank portion.

BRIEF DESCRIPTION OF THE DRAWINGS

FIG. 2B is a perspective view of a bushing of the bone anchor of FIG. 2A;

FIG. 2C is a perspective view of a saddle of the bone anchor of FIG. 2A;

FIG. 2D is a sectional side view of the saddle of FIG. 2C;

FIG. 2E is a perspective view of a drag ring of the bone anchor of FIG. 2A;

FIG. 2F is a side view of a shank of the bone anchor of FIG. 2A;

FIG. 2G is a sectional side view of a receiver member of the bone anchor of FIG. 2A;

FIG. 6G is a sectional side view of the bone anchor of FIG. 6C;

FIG. 6H is an exploded perspective view of the bone anchor of FIG. 6C;

DETAILED DESCRIPTION

Bone anchors and related methods are disclosed herein. In some embodiments, a bone anchor can include a drag interface. Exemplary drag interfaces include (i) friction between a shank and a bushing, (ii) friction between a bushing and a drag ring, (iii) friction generated by a biased saddle, and (iv) combinations of the above. The drag interface can help maintain the relative position between a receiver member and a shank of the bone anchor prior to locking the bone anchor, preventing unintended movement while still allowing free movement when intended by the user. In some embodiments, a bone anchor can include over-rotation blocking features, such as a groove, lip, or protrusion formed on a bushing of the bone anchor. Various other bone anchor features are also disclosed, including high aspect ratio drag rings and compressible drag posts.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Bone Anchor

Figure 1A:
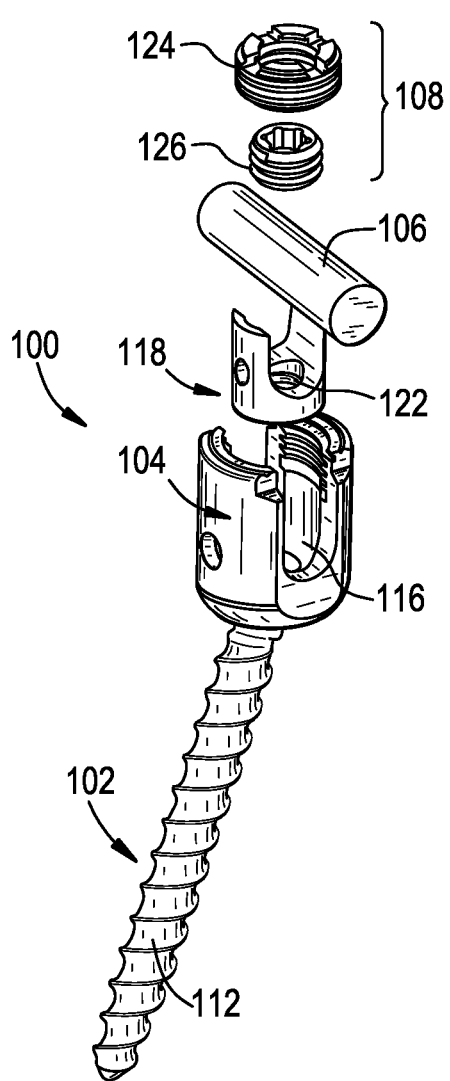
FIG. 1A is an exploded perspective view of a prior art bone anchor and a spinal rod.
Figure 1B:
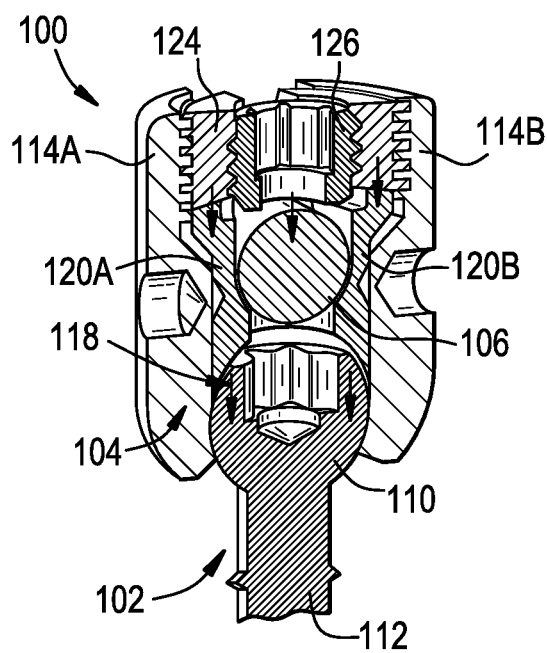
FIG. 1B is a sectional perspective view of the bone anchor of FIG. 1A.
Figure 1C:
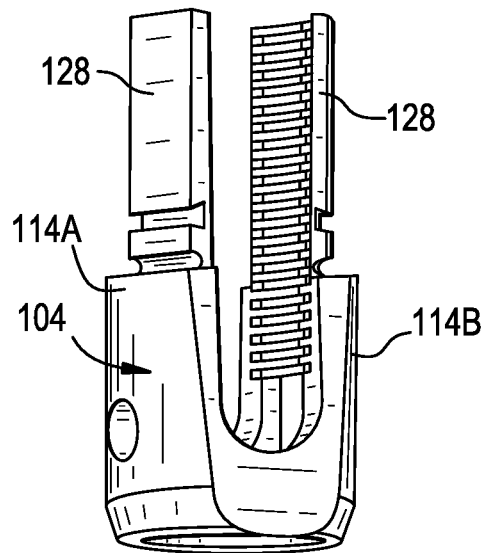
FIG. 1C is a perspective view of a receiver member of the bone anchor of FIG. 1A, shown with reduction tabs.

FIGS. 1A-1C illustrate a prior art bone anchor 100 with various features that can be included in the bone anchors 200, 300, 400, 500, 600, 700, 800, 900 described below. It will be appreciated that the illustrated bone anchor 100 is exemplary and that the bone anchors 200, 300, 400, 500, 600, 700, 800, 900 described below can include additional or alternative features.

The illustrated bone anchor 100 includes an anchor portion or shank 102, a head or receiver member 104 for receiving a spinal fixation element, such as a spinal rod 106, to be coupled to the shank 102, and a fastener or closure mechanism 108 to capture a spinal fixation element within the receiver member and fix the spinal fixation element with respect to the receiver member. The shank 102 includes a proximal head 110 and a distal shaft 112 configured to engage bone. The receiver member 104 has a proximal end having a pair of spaced apart arms 114A, 114B defining a recess or channel 116 therebetween and a distal end having a distal end surface defining an opening through which at least a portion of the shank 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the shank 102 is generally in the shape of a truncated sphere having a planar proximal surface and an approximately spherically-shaped distal surface. The illustrated bone anchor 100 is a polyaxial bone screw designed for posterior implantation in the pedicle or lateral mass of a vertebra. The proximal head 110 of the shank 102 engages the distal end of the receiver member 104 in a ball and socket like arrangement in which the proximal head and the distal shaft 112 can pivot relative to the receiver member. The distal surface of the proximal head 110 of the shank 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the shank 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the shank 102 can be cannulated, having a central passage or cannula extending the length of the shank to facilitate delivery of the shank over a guidewire in, for example, minimally-invasive procedures. Other components of the bone anchor 100, including, for example, the closure mechanism 108, the receiver member 104, and the compression cap or saddle 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the shank 102. The sidewall openings can extend radially from the cannula through the sidewall of the distal shaft 112. Exemplary systems for delivering bone cement to the bone anchor 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the shank 102 can also be coated with materials to permit bone growth, such as, for example, hydroxyapatite, and the bone anchor 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the shank 102 extends. For example, the distal shaft 112 of the shank 102 can extend through the opening.

The shank 102 can be selectively fixed relative to the receiver member 104. Prior to fixation, the shank 102 is movable relative to the receiver member 104 within a cone of angulation generally defined by the geometry of the distal end of the receiver member and the proximal head 110 of the shank 102. The bone anchor 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor 100 can be a conventional (non-biased) polyaxial screw in which the shank 102 pivots in the same amount in every direction.

The spinal fixation element, e.g., the spinal rod 106, can either directly contact the proximal head 110 of the shank 102 or can contact an intermediate element, e.g., a compression member or saddle 118. The saddle 118 can be positioned within the receiver member 104 and interposed between the spinal rod 106 and the proximal head 110 of the shank 102 to compress the distal outer surface of the proximal head into direct, fixed engagement with the distal inner surface of the receiver member 104. The saddle 118 can include a pair of spaced apart arms 120A and 120B defining a U-shaped seat 122 for receiving the spinal rod 106 and a distal surface for engaging the proximal head 110 of the shank 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the shank 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the saddle 118 and an inner set screw 126 operable to act on the rod 106. Various other closure mechanisms 108 can be used instead or in addition, such as a nut that extends around an outer circumference of the receiver member 104, a cap or fastener that slides onto the receiver member from the side, or a cap or fastener that locks to the receiver member by quarter-turn rotation. The receiver member 104 can include, can be formed integrally with, or can be coupled to one or more extension tabs 128 (shown in FIG. 1C) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor 100 can be used with a spinal fixation element such as rigid spinal rod 106. Alternatively, the spinal fixation element can be a dynamic stabilization member that allows controlled mobility between the instrumented vertebrae.

In use, the bone anchor 100 can be assembled such that the distal shaft 112 extends through the opening in the distal end of the receiver member 104 and the proximal head 110 of the shank 102 is received in the distal end of the receiver member 104. A driver instrument can be fitted with the shank 102 to drive the shank into bone. The saddle 118 can be positioned within the receiver member 104 such that the arms 120A, 120B of the saddle are aligned with the arms 114A, 114B of the receiver member 104 and the lower surface of the saddle 118 is in contact with the proximal head 110 of the shank 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the saddle 118 onto the proximal head 110 of the shank 102, thereby locking the angular position of the shank 102 relative to the receiver member 104. A torsional force can be applied to the inner set screw 126 to force the spinal rod 106 into engagement with the saddle 118 and thereby fix the spinal rod 106 relative to the receiver member 104.

The bone anchors 200, 300, 400, 500, 600, 700, 800, 900 described below can include any of the features of the bone anchors described above or other types known in the art. Exemplary bone anchors include monoaxial screws, polyaxial screws, uniplanar screws, favored-angle screws, and/or any of a variety of other bone anchor types known in the art.

Bone Anchors with Drag Features and Related Methods

FIGS. 2A-2G illustrate an exemplary embodiment of a bone anchor 200 with one or more drag features. The bone anchor 200 can include an anchor portion or shank 202, a head or receiver member 204, and a fastener or closure mechanism 208. The bone anchor 200 can also include a compression cap or saddle 218. The shank 202, receiver member 204, closure mechanism 208, and saddle 218 can include any of the features of the corresponding components of the bone anchor 100 described above. For example, as shown, the receiver member 204 can be polyaxially coupled to the head 210 of the shank 202 and can include a pair of spaced apart arms 214A, 214B defining a recess 216 therebetween. The closure mechanism 208 can be positionable between and can engage the arms 214A, 214B to capture a spinal fixation element, e.g., a spinal rod 206, within the receiver member 204, to fix the spinal fixation element with respect to the receiver member, and to fix the receiver member with respect to the shank 202. The receiver member 204 can include a central longitudinal axis A1 and the shank 202 can include a central longitudinal axis A2. The shank 202 can be rotatable relative to the receiver member 204 about the axis A2. The shank 202 can also be rotatable relative to the receiver member 204 about any of a plurality of other axes, e.g., one or more axes perpendicular to the axis A1 such as an axis A3 as shown.

A bushing 230 can be disposed between the head 210 of the shank 202 and the distal seat of the receiver member 204 to supply a first drag force. The bushing 230 can include a split to allow for radial expansion and compression of the bushing. While a split bushing is shown, the bushing 230 can include other features for allowing radial expansion and compression, such as slits, cut-outs, and the like. The exterior surface of the bushing 230 can be configured for polyaxial movement within the seat of the receiver member 204, e.g., such that the bushing can rotate about the axis A3 relative to the receiver member or about various other axes. For example, the bushing 230 can include a spherical exterior surface that engages a corresponding spherical interior surface of the receiver member 204. The interior surface of the bushing 230 can have a geometry configured to exert a drag force on the head 210 of the shank 202. For example, at least a portion of the interior surface of the bushing 230 can define a spherical surface having a resting diameter that is less than the diameter of the head 210 of the shank 202. Accordingly, once assembled to the shank 202, the bushing 230 can exert a frictional drag force against the head 210 of the shank, resisting polyaxial motion between the head of the shank and the bushing, e.g., about the axis A3.

A drag ring 232 can be disposed between the bushing 230 and the receiver member 204 to supply a second drag force. The drag ring 232 can include a split or can be C-shaped to allow for radial expansion and compression of the drag ring. The drag ring 232 can be at least partially seated within a groove or recess 234 formed in an interior surface of the receiver member 204. An inner surface of the drag ring 232 can contact and bear against the exterior surface of the bushing 230. The interior surface of the drag ring 232 can have a geometry configured to exert a drag force on the bushing 230. For example, at least a portion of the interior surface of the drag ring 232 can have a resting diameter that is less than the external diameter of the bushing 230. Accordingly, the drag ring 232 can exert a frictional drag force against the bushing 230, resisting polyaxial motion between the bushing and the receiver member 204, e.g., rotation about the axis A3. In some embodiments, the drag ring 232 can be disposed between the bushing 230 and the saddle 218. In some embodiments, the drag ring 232 can be disposed in a groove formed in the bushing 230, can move with the bushing, and can drag against the receiver member 204 and/or the saddle 218.

It will be appreciated that the relative dimensions of the bone anchor 200 components can be selected to achieve the desired drag forces, and/or to achieve the desired relative drag applied by the first drag force and the second drag force. In some embodiments, the first and second drag forces can be selected to be different, e.g., such that the shank 202 initially moves relative to the bushing 230 and only after the shank reaches maximum angulation relative to the bushing does the bushing move relative to the receiver member 204. Such an arrangement can advantageously reduce the risk of over-rotation of the bushing 230 relative to the receiver member 204, e.g., about the axis A3, which could undesirably weaken the construct. The bone anchor 200 can include additional or alternative over-rotation blocking features, including those described herein.

In use, the shank 202 of the bone anchor 200 can be driven into bone using known techniques. The receiver member 204 can then be rotated relative to the shank 202 to an initial position as desired by the user, e.g., to provisionally position the receiver member to receive a spinal rod 206. The first and/or second drag forces can maintain the receiver member 204 in this initial position prior to locking the construct, preventing the receiver member from "flopping" over. The first and second drag forces can thus prevent unintended movement prior to locking the bone anchor 200, while still allowing free movement when intended by the user. Eventually, the closure mechanism 208 can be applied to the bone anchor 200 to lock the assembly and/or to secure a spinal rod 206 within the receiver member 204.

Figure 3A:
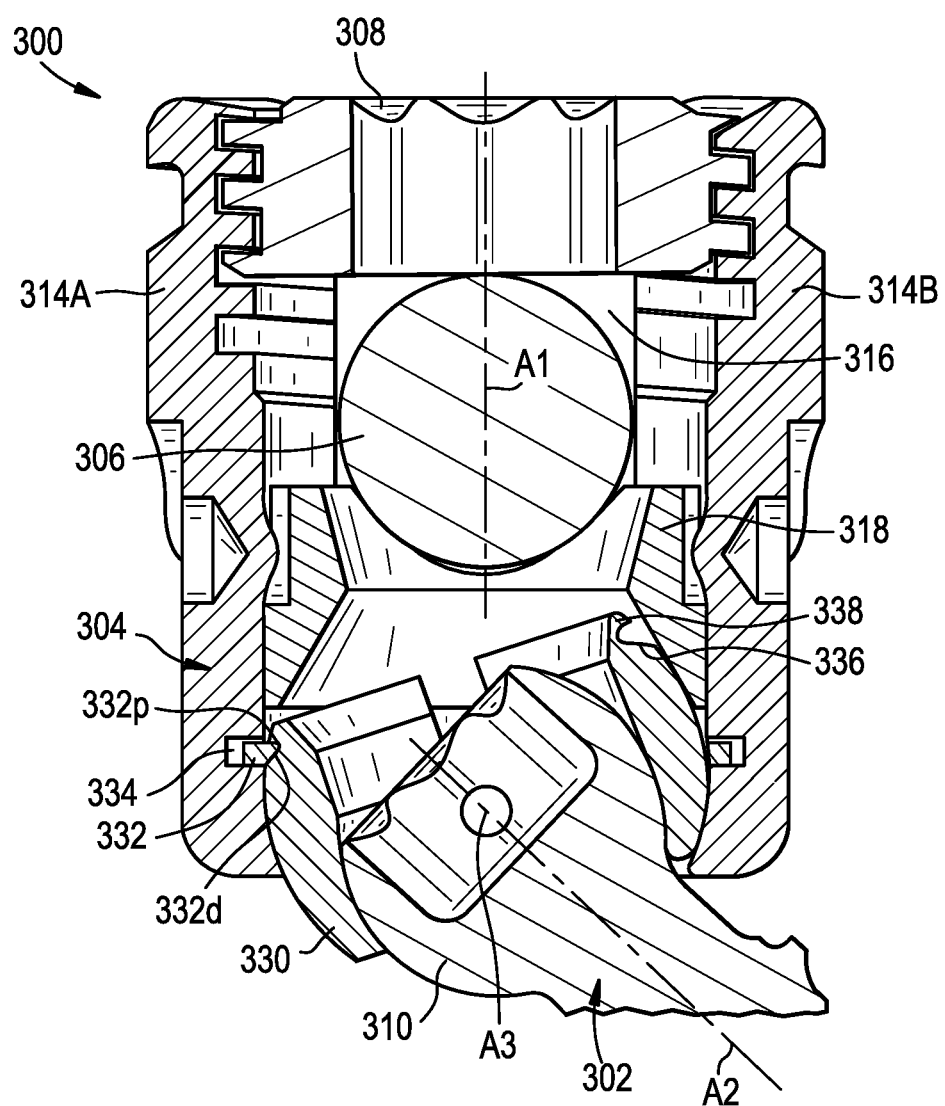
FIG. 3A is a sectional side view of a bone anchor and a spinal rod.
Figure 3B:
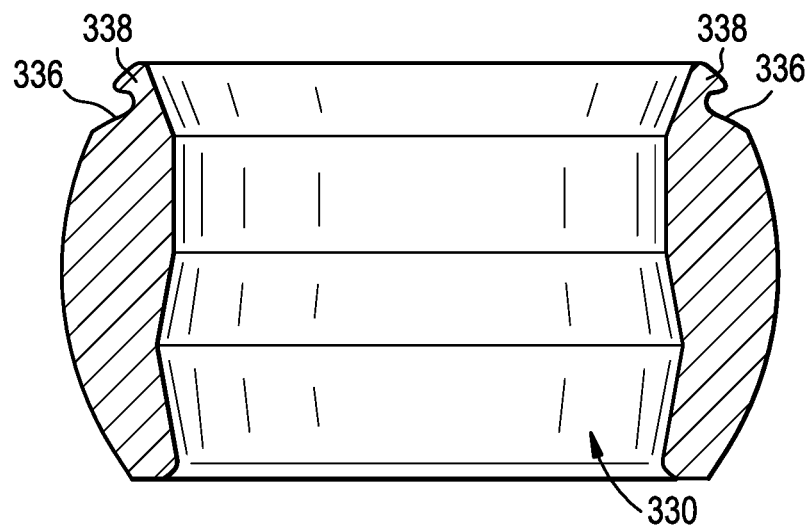
FIG. 3B is a sectional side view of a bushing of the bone anchor of FIG. 3A.
Figure 3C:
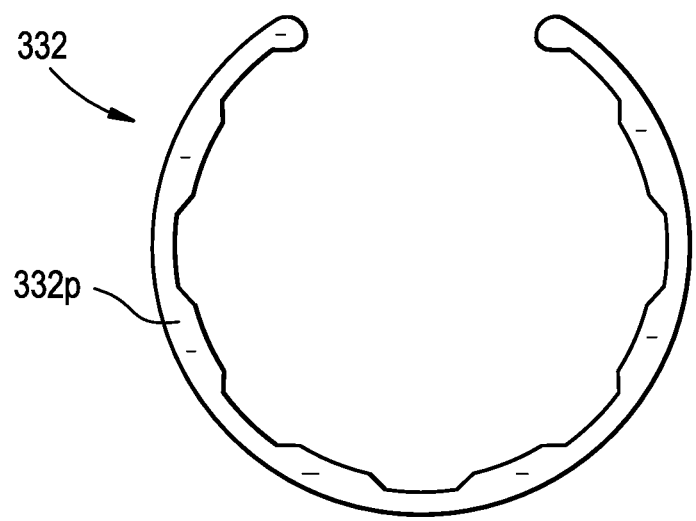
FIG. 3C is a top view of a drag ring of the bone anchor of FIG. 3A.

FIGS. 3A-3C illustrate an exemplary embodiment of a bone anchor 300 with one or more drag features. The bone anchor 300 can include an anchor portion or shank 302, a head or receiver member 304, and a fastener or closure mechanism 308. The bone anchor 300 can also include a compression cap or saddle 318. The shank 302, receiver member 304, closure mechanism 308, and saddle 318 can include any of the features of the corresponding components of the bone anchor 100 described above. For example, as shown, the receiver member 304 can be polyaxially coupled to the head 310 of the shank 302 and can include a pair of spaced apart arms 314A, 314B defining a recess 316 therebetween. The closure mechanism 308 can be positionable between and can engage the arms 314A, 314B to capture a spinal fixation element, e.g., a spinal rod 306, within the receiver member 304, to fix the spinal fixation element with respect to the receiver member, and to fix the receiver member with respect to the shank 302. The receiver member 304 can include a central longitudinal axis A1 and the shank 302 can include a central longitudinal axis A2. The shank 302 can be rotatable relative to the receiver member 304 about the axis A2. The shank 302 can also be rotatable relative to the receiver member 304 about any of a plurality of other axes, e.g., one or more axes perpendicular to the axis A1 such as an axis A3 as shown.

A bushing 330 can be disposed between the head 310 of the shank 302 and the distal seat of the receiver member 304 to supply a first drag force. The bushing 330 can include a split to allow for radial expansion and compression of the bushing. While a split bushing is shown, the bushing 330 can include other features for allowing radial expansion and compression, such as slits, cut-outs, and the like. The exterior surface of the bushing 330 can be configured for polyaxial movement within the seat of the receiver member 304, e.g., such that the bushing can rotate about the axis A3 relative to the receiver member or about various other axes. For example, the bushing 330 can include a spherical exterior surface that engages a corresponding spherical interior surface of the receiver member 304. The interior surface of the bushing 330 can have a geometry configured to exert a drag force on the head 310 of the shank 302. For example, at least a portion of the interior surface of the bushing 330 can define a spherical surface having a resting diameter that is less than the diameter of the head 310 of the shank 302. Accordingly, once assembled to the shank 302, the bushing 330 can exert a frictional drag force against the head 310 of the shank, resisting polyaxial motion between the head of the shank and the bushing, e.g., about the axis A3. The bushing 330 can include an over-rotation blocking feature. For example, the bushing 330 can include a groove 336 formed in the exterior surface of the bushing, e.g., adjacent a proximal end of the bushing. The groove 336 can define a proximal lip or shoulder 338 configured to contact a stop feature of the bone anchor 300 to prevent over-rotation of the bushing. In some embodiments, the groove 336 can be omitted and the shoulder 338 can be formed as a protrusion extending outward from the exterior surface of the bushing.

A drag ring 332 can be disposed between the bushing 330 and the receiver member 304 to supply a second drag force. The drag ring 332 can include a split or can be C-shaped to allow for radial expansion and compression of the drag ring. The drag ring 332 can be at least partially seated within a groove or recess 334 formed in an interior surface of the receiver member 304. An inner surface of the drag ring 332 can contact and bear against the exterior surface of the bushing 330. The interior surface of the drag ring 332 can have a geometry configured to exert a drag force on the bushing 330. For example, at least a portion of the interior surface of the drag ring 332 can have a resting diameter that is less than the external diameter of the bushing 330. Accordingly, the drag ring 332 can exert a frictional drag force against the bushing 330, resisting polyaxial motion between the bushing and the receiver member 304, e.g., rotation about the axis A3. The drag ring 332 can act as the stop feature that is contacted by the proximal lip 338 of the bushing 330 to prevent over-rotation of the bushing. In particular, as the bushing 330 rotates relative to the receiver member 304, e.g., about the axis A3, to a rotation limit, at least a portion of the drag ring 332 can enter the groove 336 of the bushing and contact the lip 338 to prevent further rotation of the bushing relative to the receiver member. The drag ring 332 can be shaped to facilitate locking and unlocking of the over-rotation block. For example, the drag ring 332 can include a planar proximal-facing surface 332p that extends perpendicular to the axis A1. The proximal-facing surface 332p can provide a positive stop when contacted by the lip 338 to prevent over-rotation of the bushing 330. The drag ring 332 can include a curved, ramped, or otherwise tapered distal-facing surface 332d that extends at an oblique angle relative to the axis A1. The distal-facing surface 332d of the drag ring 332 can ride along a counterpart curved, ramped, or otherwise tapered proximal-facing surface of the groove 336. This can allow the over-rotation block to be released when the bushing 330 is rotated in the opposite direction, away from the rotation limit. In particular, engagement between the tapered surfaces of the drag ring 332 and the groove 336 can cause the drag ring to expand radially out of the groove to remobilize the bushing 330 relative to the receiver member 304. The tapered surface of the drag ring 332 can be formed on one or more teeth that extend radially-inward from a circular main body of the drag ring, e.g., on a plurality of teeth spaced about the inner circumference of the main body. In some embodiments, the drag ring 332 can be disposed between the bushing 330 and the saddle 318. In some embodiments, the drag ring 332 can be disposed in a groove formed in the bushing 330, can move with the bushing, and can drag against the receiver member 304 and/or the saddle 318.

It will be appreciated that the relative dimensions of the bone anchor 300 components can be selected to achieve the desired drag forces, and/or to achieve the desired relative drag applied by the first drag force and the second drag force. In some embodiments, the first and second drag forces can be selected to be different, e.g., such that the shank 302 initially moves relative to the bushing 330 and only after the shank reaches maximum angulation relative to the bushing does the bushing move relative to the receiver member 304. Such an arrangement can advantageously reduce the risk of over-rotation of the bushing 330 relative to the receiver member 304, e.g., about the axis A3, which could undesirably weaken the construct. The bone anchor 300 can include additional or alternative over-rotation blocking features, including those described herein.

In use, the shank 302 of the bone anchor 300 can be driven into bone using known techniques. The receiver member 304 can then be rotated relative to the shank 302 to an initial position as desired by the user, e.g., to provisionally position the receiver member to receive a spinal rod 306. The first and/or second drag forces can maintain the receiver member 304 in this initial position prior to locking the construct, preventing the receiver member from "flopping" over. The first and second drag forces can thus prevent unintended movement prior to locking the bone anchor 300, while still allowing free movement when intended by the user. Eventually, the closure mechanism 308 can be applied to the bone anchor 300 to lock the assembly and/or to secure a spinal rod 306 within the receiver member 304.

Figure 4A:
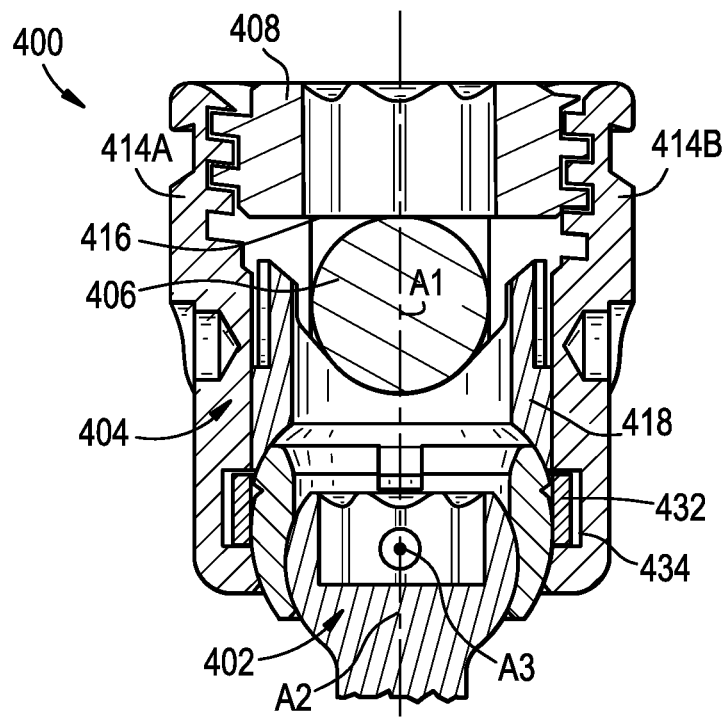
FIG. 4A is a sectional side view of a bone anchor and a spinal rod.
Figure 4B:
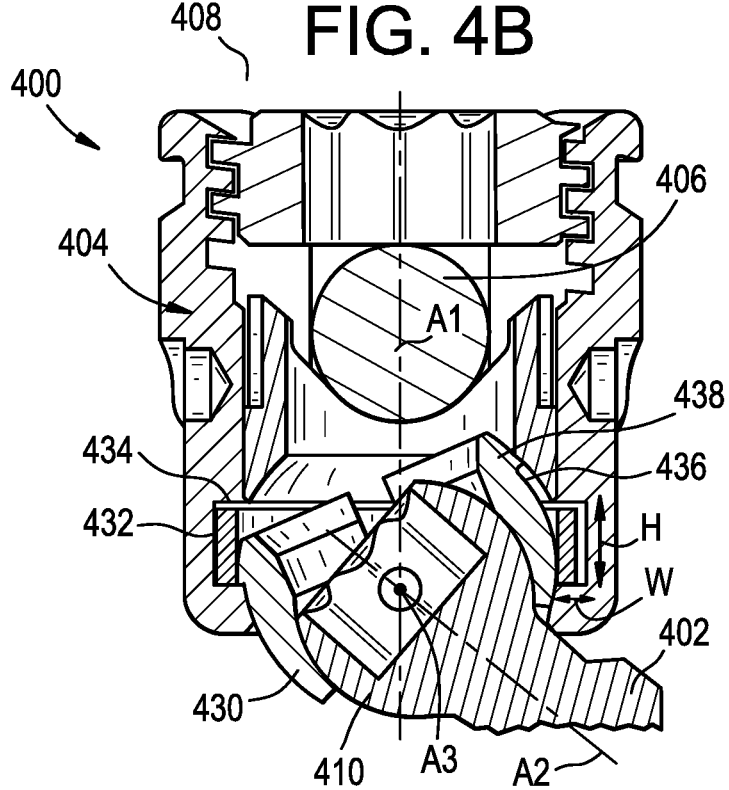
FIG. 4B is another sectional side view of the bone anchor and spinal rod of FIG. 4A.

FIGS. 4A-4B illustrate an exemplary embodiment of a bone anchor 400 with one or more drag features. The bone anchor 400 can include an anchor portion or shank 402, a head or receiver member 404, and a fastener or closure mechanism 408. The bone anchor 400 can also include a compression cap or saddle 418. The shank 402, receiver member 404, closure mechanism 408, and saddle 418 can include any of the features of the corresponding components of the bone anchor 100 described above. For example, as shown, the receiver member 404 can be polyaxially coupled to the head 410 of the shank 402 and can include a pair of spaced apart arms 414A, 414B defining a recess 416 therebetween. The closure mechanism 408 can be positionable between and can engage the arms 414A, 414B to capture a spinal fixation element, e.g., a spinal rod 406, within the receiver member 404, to fix the spinal fixation element with respect to the receiver member, and to fix the receiver member with respect to the shank 402. The receiver member 404 can include a central longitudinal axis A1 and the shank 402 can include a central longitudinal axis A2. The shank 402 can be rotatable relative to the receiver member 404 about the axis A2. The shank 402 can also be rotatable relative to the receiver member 404 about any of a plurality of other axes, e.g., one or more axes perpendicular to the axis A1 such as an axis A3 as shown.

A bushing 430 can be disposed between the head 410 of the shank 402 and the distal seat of the receiver member 404 to supply a first drag force. The bushing 430 can include a split to allow for radial expansion and compression of the bushing. While a split bushing is shown, the bushing 430 can include other features for allowing radial expansion and compression, such as slits, cut-outs, and the like. The exterior surface of the bushing 430 can be configured for polyaxial movement within the seat of the receiver member 404, e.g., such that the bushing can rotate about the axis A3 relative to the receiver member or about various other axes. For example, the bushing 430 can include a spherical exterior surface that engages a corresponding spherical interior surface of the receiver member 404. The interior surface of the bushing 430 can have a geometry configured to exert a drag force on the head 410 of the shank 402. For example, at least a portion of the interior surface of the bushing 430 can define a spherical surface having a resting diameter that is less than the diameter of the head 410 of the shank 402. Accordingly, once assembled to the shank 402, the bushing 430 can exert a frictional drag force against the head 410 of the shank, resisting polyaxial motion between the head of the shank and the bushing, e.g., about the axis A3. The bushing 430 can include an over-rotation blocking feature. For example, the bushing 430 can include a groove 436 formed in the exterior surface of the bushing, e.g., adjacent a proximal end of the bushing. The groove 436 can define a proximal lip or shoulder 438 configured to contact a stop feature of the bone anchor 400 to prevent over-rotation of the bushing. The lip 438 can have an outer diameter that is greater than an outer diameter of the portion of the bushing distal to the groove 436. In some embodiments, the groove 436 can be omitted and the lip 438 can be formed as a protrusion extending outward from the exterior surface of the bushing.

A drag ring 432 can be disposed between the bushing 430 and the receiver member 404 to supply a second drag force. The drag ring 432 can include a split or can be C-shaped to allow for radial expansion and compression of the drag ring. The drag ring 432 can be at least partially seated within a groove or recess 434 formed in an interior surface of the receiver member 404. An inner surface of the drag ring 432 can contact and bear against the exterior surface of the bushing 430. The interior surface of the drag ring 432 can have a geometry configured to exert a drag force on the bushing 430. For example, at least a portion of the interior surface of the drag ring 432 can have a resting diameter that is less than the external diameter of the bushing 430. Accordingly, the drag ring 432 can exert a frictional drag force against the bushing 430, resisting polyaxial motion between the bushing and the receiver member 404, e.g., rotation about the axis A3. In some embodiments, the drag ring 432 can be disposed between the bushing 430 and the saddle 418. In some embodiments, the drag ring 432 can be disposed in a groove formed in the bushing 430, can move with the bushing, and can drag against the receiver member 404 and/or the saddle 418.

The recess 434 formed in the receiver member 404 can act as the stop feature that is contacted by the proximal lip 438 of the bushing 430 to prevent over-rotation of the bushing. In particular, as the bushing 430 rotates relative to the receiver member 404, e.g., about the axis A3, to a rotation limit, the lip 438 can contact the distal floor of the recess 434 to prevent further rotation of the bushing relative to the receiver member.

It will be appreciated that the relative dimensions of the bone anchor 400 components can be selected to achieve the desired drag forces, and/or to achieve the desired relative drag applied by the first drag force and the second drag force. In some embodiments, the first and second drag forces can be selected to be different, e.g., such that the shank 402 initially moves relative to the bushing 430 and only after the shank reaches maximum angulation relative to the bushing does the bushing move relative to the receiver member 404. Such an arrangement can advantageously reduce the risk of over-rotation of the bushing 430 relative to the receiver member 404, e.g., about the axis A3, which could undesirably weaken the construct. The bone anchor 400 can include additional or alternative over-rotation blocking features, including those described herein.

In use, the shank 402 of the bone anchor 400 can be driven into bone using known techniques. The receiver member 404 can then be rotated relative to the shank 402 to an initial position as desired by the user, e.g., to provisionally position the receiver member to receive a spinal rod 406. The first and/or second drag forces can maintain the receiver member 404 in this initial position prior to locking the construct, preventing the receiver member from "flopping" over. The first and second drag forces can thus prevent unintended movement prior to locking the bone anchor 400, while still allowing free movement when intended by the user. Eventually, the closure mechanism 408 can be applied to the bone anchor 400 to lock the assembly and/or to secure a spinal rod 406 within the receiver member 404.

FIGS. 5A-5H illustrate an exemplary embodiment of a bone anchor 500 with one or more drag features. The bone anchor 500 can include an anchor portion or shank 502, a head or receiver member 504, and a fastener or closure mechanism 508. The bone anchor 500 can also include a compression cap or saddle 518. The shank 502, receiver member 504, closure mechanism 508, and saddle 518 can include any of the features of the corresponding components of the bone anchor 100 described above. For example, as shown, the receiver member 504 can be polyaxially coupled to the head 510 of the shank 502 and can include a pair of spaced apart arms 514A, 514B defining a recess 516 therebetween. The closure mechanism 508 can be positionable between and can engage the arms 514A, 514B to capture a spinal fixation element, e.g., a spinal rod 506, within the receiver member 504, to fix the spinal fixation element with respect to the receiver member, and to fix the receiver member with respect to the shank 502. The receiver member 504 can include a central longitudinal axis A1 and the shank 502 can include a central longitudinal axis A2. The shank 502 can be rotatable relative to the receiver member 504 about the axis A2. The shank 502 can also be rotatable relative to the receiver member 504 about any of a plurality of other axes, e.g., one or more axes perpendicular to the axis A1 such as an axis A3 as shown.

A bushing 530 can be disposed between the head 510 of the shank 502 and the distal seat of the receiver member 504 to supply a first drag force. The bushing 530 can include a split to allow for radial expansion and compression of the bushing. While a split bushing is shown, the bushing 530 can include other features for allowing radial expansion and compression, such as slits, cut-outs, and the like. The exterior surface of the bushing 530 can be configured for polyaxial movement within the seat of the receiver member 504, e.g., such that the bushing can rotate about the axis A3 relative to the receiver member or about various other axes. For example, the bushing 530 can include a spherical exterior surface that engages a corresponding spherical interior surface of the receiver member 504. The interior surface of the bushing 530 can have a geometry configured to exert a drag force on the head 510 of the shank 502. For example, at least a portion of the interior surface of the bushing 530 can define a spherical surface having a resting diameter that is less than the diameter of the head 510 of the shank 502. Accordingly, once assembled to the shank 502, the bushing 530 can exert a frictional drag force against the head 510 of the shank, resisting polyaxial motion between the head of the shank and the bushing, e.g., about the axis A3. The bushing 530 can include an over-rotation blocking feature. For example, the bushing 530 can include a proximal lip or shoulder 538 configured to contact a stop feature of the bone anchor 500 to prevent over-rotation of the bushing. The lip 538 can have an outer diameter that is greater than an outer diameter of a distal portion of the bushing. In some embodiments, the lip 538 can be formed by a groove formed in the exterior surface of the bushing 530.

The distal seat formed in the receiver member 504 can act as the stop feature that is contacted by the proximal lip 538 of the bushing 530 to prevent over-rotation of the bushing. In particular, as the bushing 530 rotates relative to the receiver member 504, e.g., about the axis A3, to a rotation limit, the lip 538 can contact the distal seat to prevent further rotation of the bushing relative to the receiver member.

A ring 532 can be disposed between the saddle 518 and the receiver member 504 to supply a second drag force. The ring 532 can include a split or can be C-shaped to allow for radial expansion and compression of the ring. The ring 532 can be at least partially seated within a groove or recess 534A formed in an interior surface of the receiver member 504 and at least partially seated within a groove or recess 534B formed in an exterior surface of the saddle 518. The ring 532 can be formed from a resilient material. The ring 532 can have a resting diameter that is greater than a diameter of the recess 534A. Accordingly, the ring 532 can be biased radially outward to exert a spring force against a lateral sidewall 540 of the recess 534A. The lateral sidewall 540 can be ramped, curved, or otherwise tapered. For example, as shown, the lateral sidewall 540 can have a diameter at a proximal end thereof that is less than a diameter at a distal end thereof. The lateral sidewall 540 can be defined by a conical surface. As the ring 532 expands radially outward against the lateral sidewall 540, the ring 532 can be urged distally along the axis A1. This distal movement of the ring 532 can cause corresponding distal movement of the saddle 518 along the axis A1 by virtue of the ring 532 being at least partially received within the recess 534B of the saddle. Accordingly, the lateral sidewall 540 can be effective to convert the radially-outwardly applied bias force of the ring 532 into a distally-directed force applied by the saddle 518 to the bushing 530 or, in embodiments in which the bushing is omitted, to the head 510 of the shank 502. Urging of the saddle 518 distally can thus supply a second drag force, resisting polyaxial motion between the bushing and the receiver member 504, e.g., rotation about the axis A3. In some embodiments, the groove 534B can include a ramped surface and the ring 532 can be biased radially-inward against said surface to urge the saddle 518 distally.

It will be appreciated that the relative dimensions of the bone anchor 500 components can be selected to achieve the desired drag forces, and/or to achieve the desired relative drag applied by the first drag force and the second drag force. In some embodiments, the first and second drag forces can be selected to be different, e.g., such that the shank 502 initially moves relative to the bushing 530 and only after the shank reaches maximum angulation relative to the bushing does the bushing move relative to the receiver member 504. Such an arrangement can advantageously reduce the risk of over-rotation of the bushing 530 relative to the receiver member 504, e.g., about the axis A3, which could undesirably weaken the construct. The bone anchor 500 can include additional or alternative over-rotation blocking features, including those described herein.

Figure 5A:
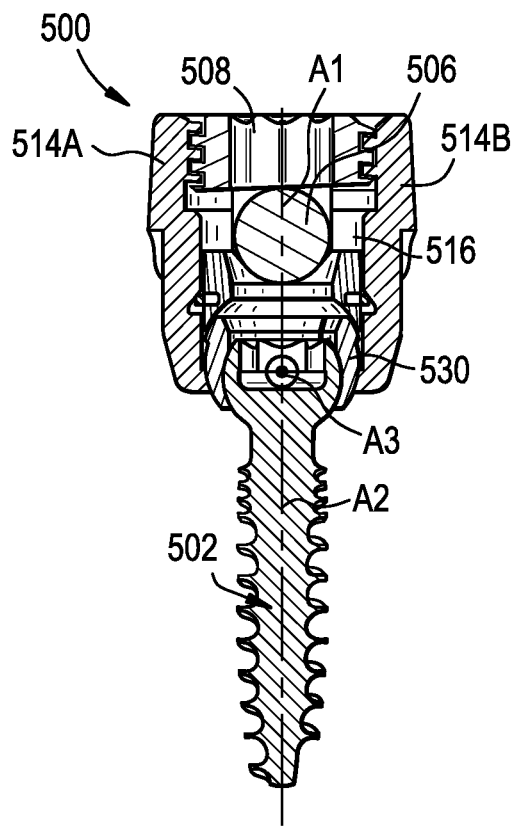
FIG. 5A is a sectional side view of a bone anchor and a spinal rod.
Figure 5B:
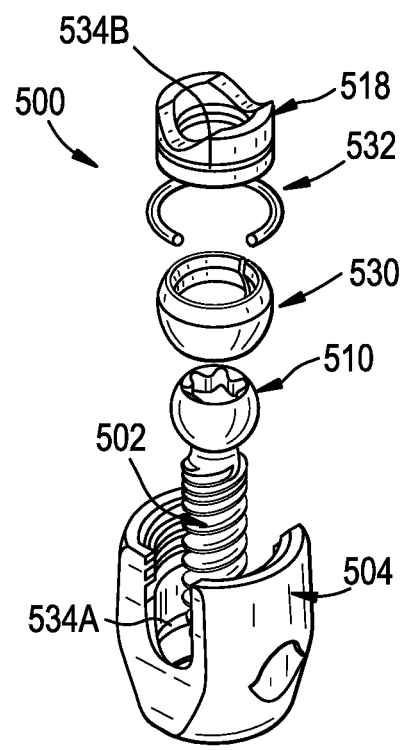
FIG. 5B is an exploded perspective view of the bone anchor of FIG. 5A.
Figure 5C:
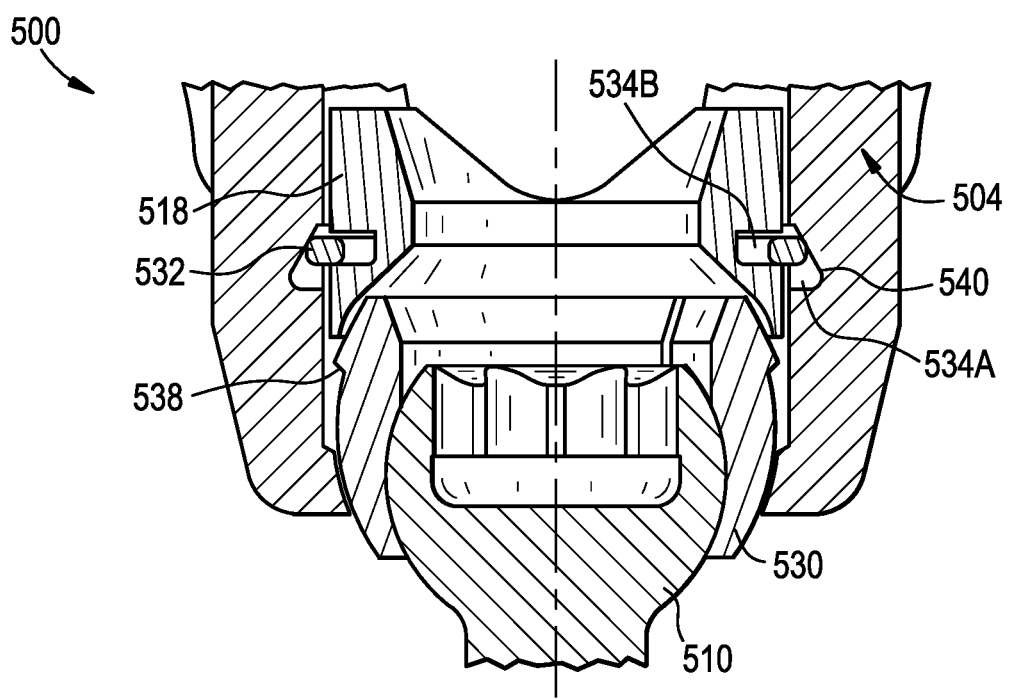
FIG. 5C is a close-up sectional side view of the bone anchor of FIG. 5A.
Figure 5D:
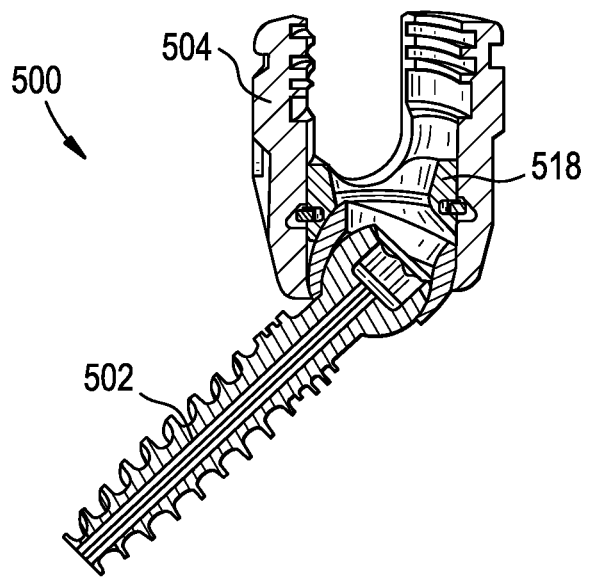
FIG. 5D is a sectional perspective view of the bone anchor of FIG. 5A.
Figure 5E:
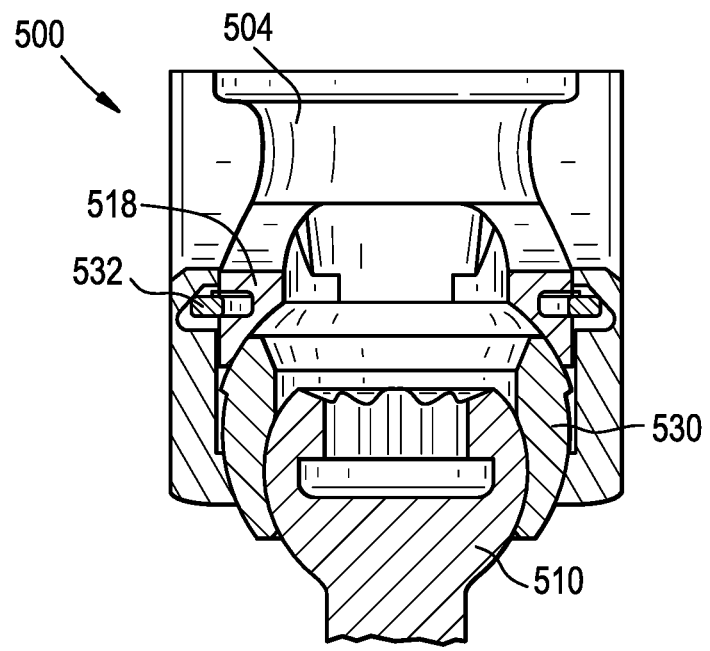
FIG. 5E is a sectional side view of the bone anchor of FIG. 5A.
Figure 5F:
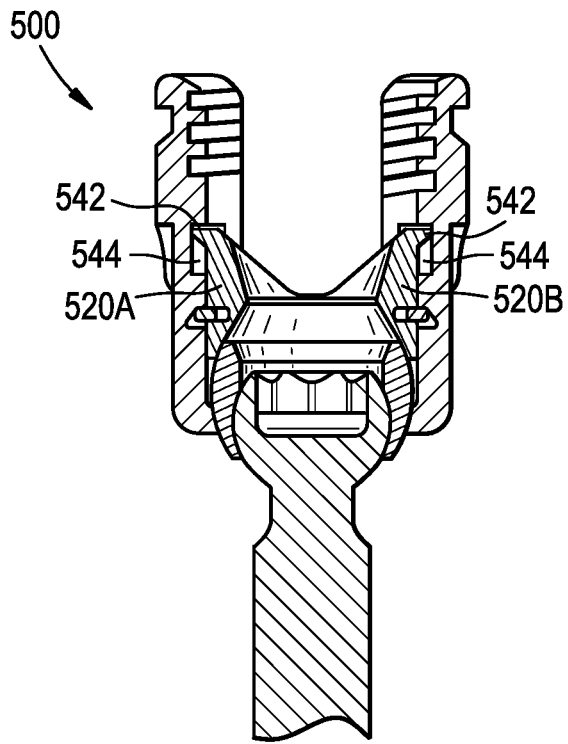
FIG. 5F is a sectional side view of the bone anchor of FIG. 5A, shown with a saddle having anti-rotation features.
Figure 5G:
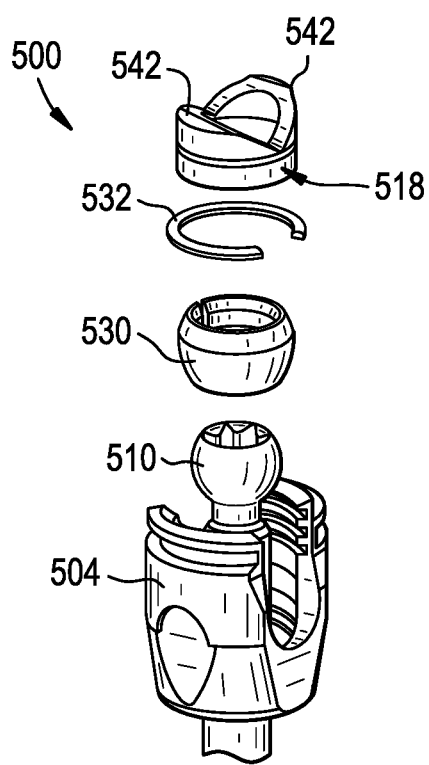
FIG. 5G is an exploded perspective view of the bone anchor of FIG. 5F.
Figure 5H:
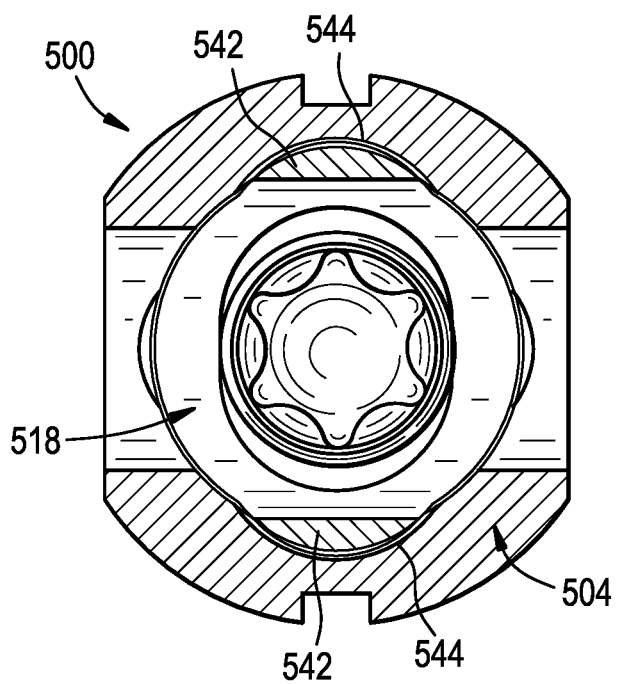
FIG. 5H is a sectional top view of the bone anchor of FIG. 5F.
Figure 6A:
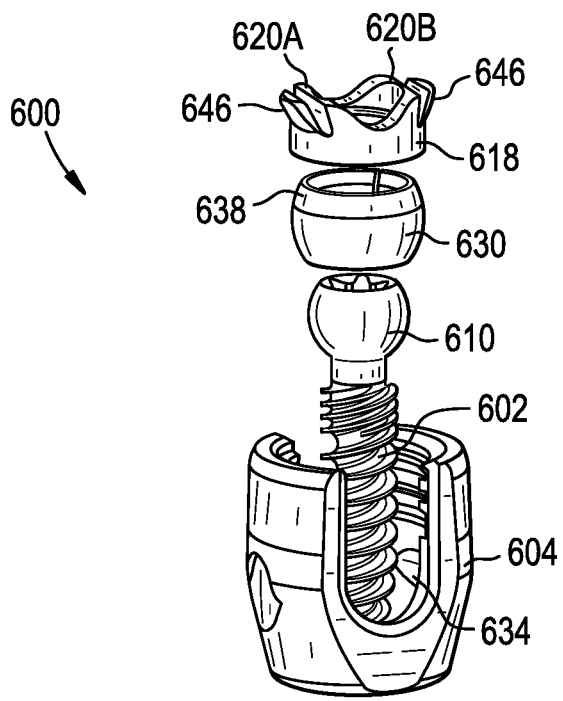
FIG. 6A is an exploded perspective view of a bone anchor.
Figure 6B:
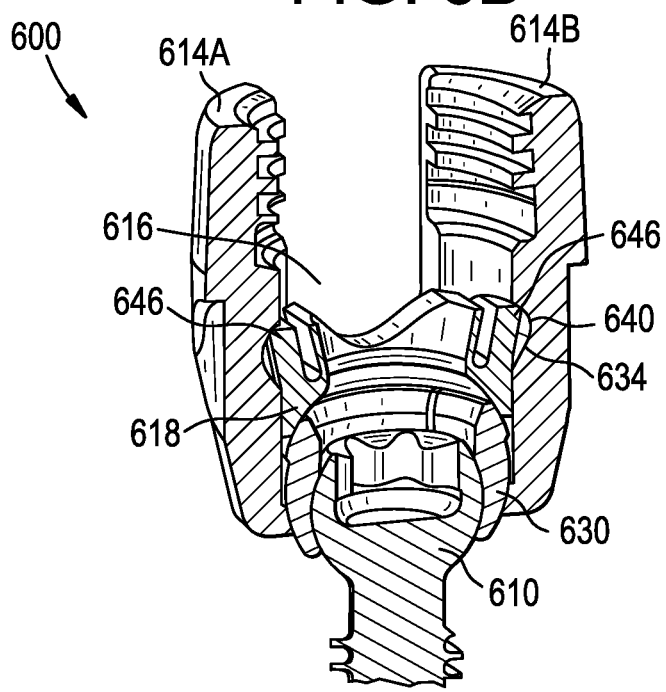
FIG. 6B is a sectional perspective view of the bone anchor of FIG. 6A.
Figure 6C:
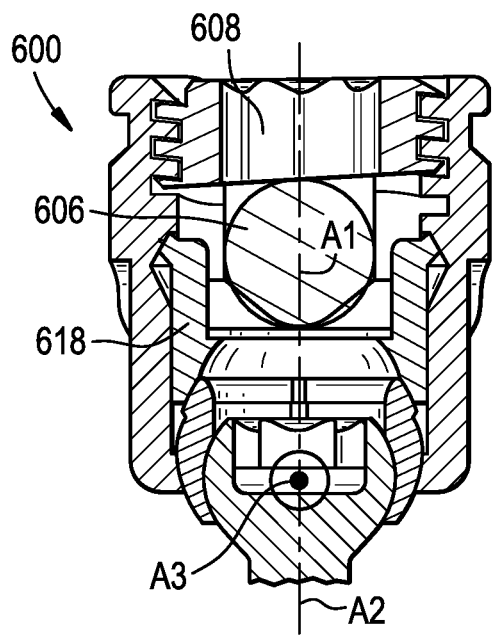
FIG. 6C is a sectional side view of the bone anchor of FIG. 6A and a spinal rod, shown with a saddle having alternative ears.
Figure 6D:
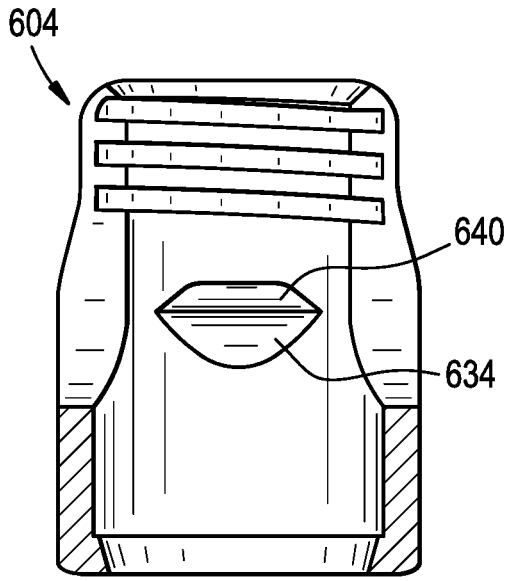
FIG. 6D is a sectional side view of a receiver member of the bone anchor of FIG. 6A.
Figure 6E:
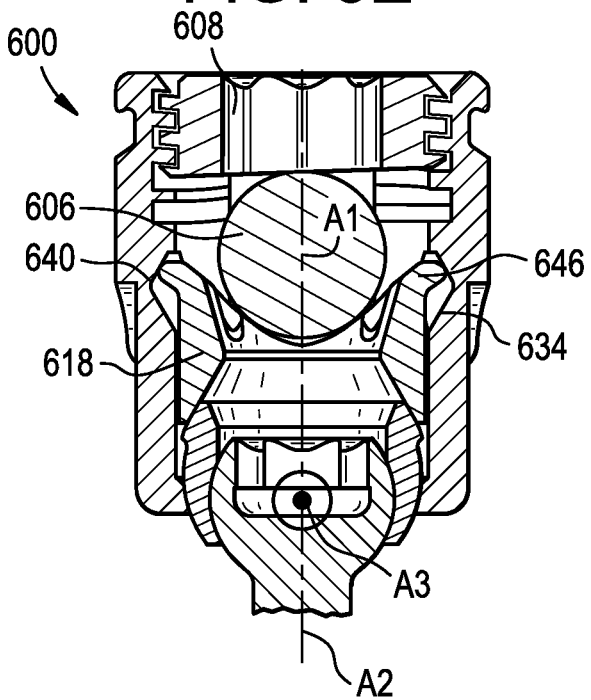
FIG. 6E is a sectional side view of the bone anchor and spinal rod of FIG. 6C.
Figure 6F:
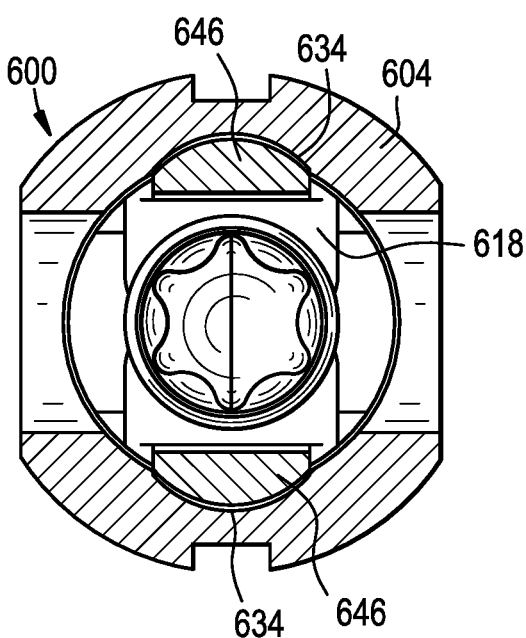
FIG. 6F is a sectional top view of the bone anchor of FIG. 6C.

In some embodiments, as shown in FIGS. 5F-5H, the saddle 518 can include anti-rotation features to limit or prevent rotation of the saddle 518 relative to the receiver member 504 about the axis A1. For example, the arms 520A, 520B of the saddle 518 can include male projections 542 that extend radially-outward from the proximal ends of the arms. The projections 542 can be received within corresponding keyways 544 formed in the receiver member 504, such that rotation of the saddle 518 relative to the receiver member about the axis A1 is limited or prevented. This engagement between the projections 542 and the keyways 544 can also be effective to retain the saddle 518 within the receiver member 504.

In use, the shank 502 of the bone anchor 500 can be driven into bone using known techniques. The receiver member 504 can then be rotated relative to the shank 502 to an initial position as desired by the user, e.g., to provisionally position the receiver member to receive a spinal rod 506. The first and/or second drag forces can maintain the receiver member 504 in this initial position prior to locking the construct, preventing the receiver member from "flopping" over. The first and second drag forces can thus prevent unintended movement prior to locking the bone anchor 500, while still allowing free movement when intended by the user. Eventually, the closure mechanism 508 can be applied to the bone anchor 500 to lock the assembly and/or to secure a spinal rod 506 within the receiver member 504.

FIGS. 6A-6H illustrate an exemplary embodiment of a bone anchor 600 with one or more drag features. The bone anchor 600 can include an anchor portion or shank 602, a head or receiver member 604, and a fastener or closure mechanism 608. The bone anchor 600 can also include a compression cap or saddle 618. The shank 602, receiver member 604, closure mechanism 608, and saddle 618 can include any of the features of the corresponding components of the bone anchor 100 described above. For example, as shown, the receiver member 604 can be polyaxially coupled to the head 610 of the shank 602 and can include a pair of spaced apart arms 614A, 614B defining a recess 616 therebetween. The closure mechanism 608 can be positionable between and can engage the arms 614A, 614B to capture a spinal fixation element, e.g., a spinal rod 606, within the receiver member 604, to fix the spinal fixation element with respect to the receiver member, and to fix the receiver member with respect to the shank 602. The receiver member 604 can include a central longitudinal axis A1 and the shank 602 can include a central longitudinal axis A2. The shank 602 can be rotatable relative to the receiver member 604 about the axis A2. The shank 602 can also be rotatable relative to the receiver member 604 about any of a plurality of other axes, e.g., one or more axes perpendicular to the axis A1 such as an axis A3 as shown.

A bushing 630 can be disposed between the head 610 of the shank 602 and the distal seat of the receiver member 604 to supply a first drag force. The bushing 630 can include a split to allow for radial expansion and compression of the bushing. While a split bushing is shown, the bushing 630 can include other features for allowing radial expansion and compression, such as slits, cut-outs, and the like. The exterior surface of the bushing 630 can be configured for polyaxial movement within the seat of the receiver member 604, e.g., such that the bushing can rotate about the axis A3 relative to the receiver member or about various other axes. For example, the bushing 630 can include a spherical exterior surface that engages a corresponding spherical interior surface of the receiver member 604. The interior surface of the bushing 630 can have a geometry configured to exert a drag force on the head 610 of the shank 602. For example, at least a portion of the interior surface of the bushing 630 can define a spherical surface having a resting diameter that is less than the diameter of the head 610 of the shank 602. Accordingly, once assembled to the shank 602, the bushing 630 can exert a frictional drag force against the head 610 of the shank, resisting polyaxial motion between the head of the shank and the bushing, e.g., about the axis A3. The bushing 630 can include an over-rotation blocking feature. For example, the bushing 630 can include a proximal lip or shoulder 638 configured to contact a stop feature of the bone anchor 600 to prevent over-rotation of the bushing. The lip 638 can have an outer diameter that is greater than an outer diameter of a distal portion of the bushing. In some embodiments, the lip 638 can be formed by a groove formed in the exterior surface of the bushing 630.

The distal seat formed in the receiver member 604 can act as the stop feature that is contacted by the proximal lip 638 of the bushing 630 to prevent over-rotation of the bushing. In particular, as the bushing 630 rotates relative to the receiver member 604, e.g., about the axis A3, to a rotation limit, the lip 638 can contact the distal seat to prevent further rotation of the bushing relative to the receiver member.

The saddle 618 can include one or more spring tabs or ears 646 configured to engage the receiver member 604 to supply a second drag force. The ears 646 can be at least partially seated within a groove or recess 634 formed in an interior surface of the receiver member 604. The ears 646 can project radially outward from the arms 620A, 620B of the saddle 618, e.g., as shown in FIGS. 6C-6H. In such arrangements, as shown, slits can be formed in the saddle 618 between the arms 620A, 620B and the rod seat to allow the arms to deform or deflect radially without deforming the rod seat. In other arrangements, as shown for example in FIGS. 6A-6B, the ears 646 can be formed as a second set of arms extending alongside the arms 620A, 620B and disposed radially-outward therefrom. The ears 646 can be formed from a resilient material. The ears can have a resting diameter or outer dimension that is greater than a diameter of the recess 634. Accordingly, the ears 646 can be biased radially outward to exert a spring force against a lateral sidewall 640 of the recess 634. The lateral sidewall 640 can be ramped, curved, or otherwise tapered. For example, as shown, the lateral sidewall 640 can have a diameter at a proximal end thereof that is less than a diameter at a middle portion thereof. The lateral sidewall 640 can be defined at least in part by a conical surface. As the ears 646 expand radially outward against the lateral sidewall 640, the saddle 618 can be urged distally along the axis A1. Accordingly, the lateral sidewall 640 can be effective to convert the radially-outwardly applied bias force of the ears 646 into a distally-directed force applied by the saddle 618 to the bushing 630 or, in embodiments in which the bushing is omitted, to the head 610 of the shank 602. Urging of the saddle 618 distally can thus supply a second drag force, resisting polyaxial motion between the bushing and the receiver member 604, e.g., rotation about the axis A3. In some embodiments, the ears can be formed on the receiver member 604 and can be biased radially-inward against ramped surfaces of the saddle 618.

It will be appreciated that the relative dimensions of the bone anchor 600 components can be selected to achieve the desired drag forces, and/or to achieve the desired relative drag applied by the first drag force and the second drag force. In some embodiments, the first and second drag forces can be selected to be different, e.g., such that the shank 602 initially moves relative to the bushing 630 and only after the shank reaches maximum angulation relative to the bushing does the bushing move relative to the receiver member 604. Such an arrangement can advantageously reduce the risk of over-rotation of the bushing 630 relative to the receiver member 604, e.g., about the axis A3, which could undesirably weaken the construct. The bone anchor 600 can include additional or alternative over-rotation blocking features, including those described herein.

In some embodiments, the saddle 618 can include anti-rotation features to limit or prevent rotation of the saddle relative to the receiver member 604 about the axis A1. For example, the recess 634 of the receiver member 604 can be formed as first and second opposed recesses having limited circumferential widths, such that receipt of the ears 646 within the recesses is effective to limit or prevent rotation of the saddle 618 relative to the receiver member about the axis A1. This engagement between the ears 646 and the recesses 634 can also be effective to retain the saddle 618 within the receiver member 604.

In use, the shank 602 of the bone anchor 600 can be driven into bone using known techniques. The receiver member 604 can then be rotated relative to the shank 602 to an initial position as desired by the user, e.g., to provisionally position the receiver member to receive a spinal rod 606. The first and/or second drag forces can maintain the receiver member 604 in this initial position prior to locking the construct, preventing the receiver member from "flopping" over. The first and second drag forces can thus prevent unintended movement prior to locking the bone anchor 600, while still allowing free movement when intended by the user. Eventually, the closure mechanism 608 can be applied to the bone anchor 600 to lock the assembly and/or to secure a spinal rod 606 within the receiver member 604.

Figure 7:
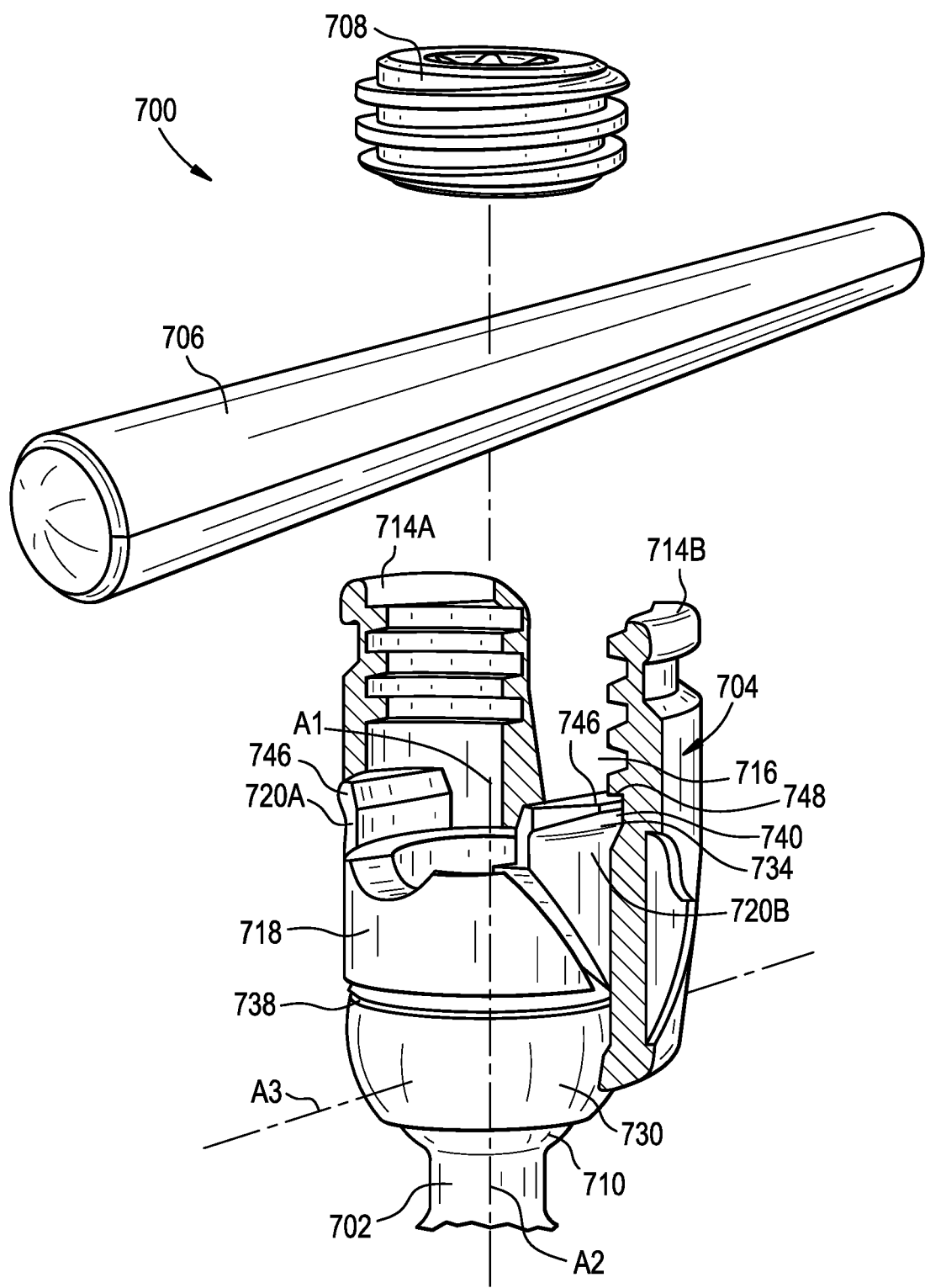
FIG. 7 is a partially-exploded, partially-sectional perspective view of a bone anchor and a spinal rod.

FIG. 7 illustrates an exemplary embodiment of a bone anchor 700 with one or more drag features. The bone anchor 700 can include an anchor portion or shank 702, a head or receiver member 704, and a fastener or closure mechanism 708. The bone anchor 700 can also include a compression cap or saddle 718. The shank 702, receiver member 704, closure mechanism 708, and saddle 718 can include any of the features of the corresponding components of the bone anchor 100 described above. For example, as shown, the receiver member 704 can be polyaxially coupled to the head 710 of the shank 702 and can include a pair of spaced apart arms 714A, 714B defining a recess 716 therebetween. The closure mechanism 708 can be positionable between and can engage the arms 714A, 714B to capture a spinal fixation element, e.g., a spinal rod 706, within the receiver member 704, to fix the spinal fixation element with respect to the receiver member, and to fix the receiver member with respect to the shank 702. The receiver member 704 can include a central longitudinal axis A1 and the shank 702 can include a central longitudinal axis A2. The shank 702 can also be rotatable relative to the receiver member 704 about any of a plurality of other axes, e.g., one or more axes perpendicular to the axis A1 such as an axis A3 as shown.

A bushing 730 can be disposed between the head 710 of the shank 702 and the distal seat of the receiver member 704 to supply a first drag force. The bushing 730 can include a split to allow for radial expansion and compression of the bushing. While a split bushing is shown, the bushing 730 can include other features for allowing radial expansion and compression, such as slits, cut-outs, and the like. The exterior surface of the bushing 730 can be configured for polyaxial movement within the seat of the receiver member 704, e.g., such that the bushing can rotate about the axis A3 relative to the receiver member or about various other axes. For example, the bushing 730 can include a spherical exterior surface that engages a corresponding spherical interior surface of the receiver member 704. The interior surface of the bushing 730 can have a geometry configured to exert a drag force on the head 710 of the shank 702. For example, at least a portion of the interior surface of the bushing 730 can define a spherical surface having a resting diameter that is less than the diameter of the head 710 of the shank 702. Accordingly, once assembled to the shank 702, the bushing 730 can exert a frictional drag force against the head 710 of the shank, resisting polyaxial motion between the head of the shank and the bushing, e.g., about the axis A3. The bushing 730 can include an over-rotation blocking feature. For example, the bushing 730 can include a proximal lip or shoulder 738 configured to contact a stop feature of the bone anchor 700 to prevent over-rotation of the bushing. The lip 738 can have an outer diameter that is greater than an outer diameter of a distal portion of the bushing. In some embodiments, the lip 738 can be formed by a groove formed in the exterior surface of the bushing 730.

The distal seat formed in the receiver member 704 can act as the stop feature that is contacted by the proximal lip 738 of the bushing 730 to prevent over-rotation of the bushing. In particular, as the bushing 730 rotates relative to the receiver member 704, e.g., about the axis A3, to a rotation limit, the lip 738 can contact the distal seat to prevent further rotation of the bushing relative to the receiver member.

The saddle 718 can be biased to expand, e.g., radially-outward, to supply a second drag force. The saddle 718 can include one or more splits or slits formed in the sidewall of the saddle to allow the saddle to be compressed and expanded radially. For example, the illustrated saddle 718 includes a split that extends at an oblique angle relative to the axis A1. The saddle 718 can include one or more protrusions 746 configured to engage the receiver member 704 to supply a second drag force. The protrusions 746 can be at least partially seated within a groove or recess 734 formed in an interior surface of the receiver member 704. The protrusions 746 can project radially outward from the arms 720A, 720B of the saddle 718. The saddle 718 and, in particular, the protrusions 746 can have a resting diameter or outer dimension that is greater than a diameter of the recess 734. Accordingly, the protrusions 746 can be biased radially outward to exert a spring force against a lateral sidewall 740 of the recess 734. The lateral sidewall 740 can be ramped, curved, or otherwise tapered. For example, as shown, the lateral sidewall 740 can have a diameter at a proximal end thereof that is less than a diameter at a middle portion thereof. The lateral sidewall 740 can be defined at least in part by a conical surface. As the protrusions 746 expand radially outward against the lateral sidewall 740, the saddle 718 can be urged distally along the axis A1. Accordingly, the lateral sidewall 740 can be effective to convert the radially-outwardly applied bias force of the expanding saddle 718 into a distally-directed force applied by the saddle 718 to the bushing 730 or, in embodiments in which the bushing is omitted, to the head 710 of the shank 702. Urging of the saddle 718 distally can thus supply a second drag force, resisting polyaxial motion between the bushing and the receiver member 704, e.g., rotation about the axis A3.

Alternatively, or in addition, the saddle 718 can be biased to expand longitudinally along the axis A1 to supply the second drag force. The saddle 718 can include one or more splits or slits formed in the sidewall of the saddle to allow the saddle to be compressed and expanded longitudinally. For example, the saddle 718 can include a split that extends at an oblique angle relative to the axis A1. When installed in the receiver member 704, distal travel of the saddle 718 can be limited by contact with the bushing 730 or, in embodiments in which the bushing is omitted, with the head 710 of the shank 702. Also when installed in the receiver member 704, proximal travel of the saddle 718 can be limited by contact with a ledge or shoulder 748 of the receiver member, e.g., defined by a proximal roof of the groove 734. The longitudinal spacing between the shoulder 748 and the bushing 730 (or the head 710) can be less than the resting longitudinal dimension of the saddle 718. Accordingly, when disposed between the shoulder 748 and the bushing 730 (or the head 710), the saddle 718 is compressed from its resting state. Resilient material properties of the saddle 718 can thereby cause the saddle to exert a distal biasing force against the bushing 730 (or the head 710) substantially along the axis A1. The saddle 718 can thus supply a second drag force, resisting polyaxial motion between the bushing 730 and the receiver member 704, e.g., rotation about the axis A3.

It will be appreciated that the relative dimensions of the bone anchor 700 components can be selected to achieve the desired drag forces, and/or to achieve the desired relative drag applied by the first drag force and the second drag force. In some embodiments, the first and second drag forces can be selected to be different, e.g., such that the shank 702 initially moves relative to the bushing 730 and only after the shank reaches maximum angulation relative to the bushing does the bushing move relative to the receiver member 704. Such an arrangement can advantageously reduce the risk of over-rotation of the bushing 730 relative to the receiver member 704, e.g., about the axis A3, which could undesirably weaken the construct. The bone anchor 700 can include additional or alternative over-rotation blocking features, including those described herein.

In some embodiments, the saddle 718 can include anti-rotation features to limit or prevent rotation of the saddle relative to the receiver member 704 about the axis A1. For example, the recess 734 of the receiver member 704 can be formed as first and second opposed recesses having limited circumferential widths, such that receipt of the protrusions 746 within the recesses is effective to limit or prevent rotation of the saddle 718 relative to the receiver member about the axis A1. This engagement between the protrusions 746 and the recesses 734 can also be effective to retain the saddle 718 within the receiver member 704.

In use, the shank 702 of the bone anchor 700 can be driven into bone using known techniques. The receiver member 704 can then be rotated relative to the shank 702 to an initial position as desired by the user, e.g., to provisionally position the receiver member to receive a spinal rod 706. The first and/or second drag forces can maintain the receiver member 704 in this initial position prior to locking the construct, preventing the receiver member from "flopping" over. The first and second drag forces can thus prevent unintended movement prior to locking the bone anchor 700, while still allowing free movement when intended by the user. Eventually, the closure mechanism 708 can be applied to the bone anchor 700 to lock the assembly and/or to secure a spinal rod 706 within the receiver member 704.

FIGS. 8A-8H illustrate an exemplary embodiment of a bone anchor 800 with one or more drag features. The bone anchor 800 can include an anchor portion or shank 802, a head or receiver member 804, and a fastener or closure mechanism 808. The bone anchor 800 can also include a compression cap or saddle 818. The shank 802, receiver member 804, closure mechanism 808, and saddle 818 can include any of the features of the corresponding components of the bone anchor 100 described above. For example, as shown, the receiver member 804 can be polyaxially coupled to the head 810 of the shank 802 and can include a pair of spaced apart arms 814A, 814B defining a recess 816 therebetween. The closure mechanism 808 can be positionable between and can engage the arms 814A, 814B to capture a spinal fixation element, e.g., a spinal rod 806, within the receiver member 804, to fix the spinal fixation element with respect to the receiver member, and to fix the receiver member with respect to the shank 802. The receiver member 804 can include a central longitudinal axis A1 and the shank 802 can include a central longitudinal axis A2. The shank 802 can be rotatable relative to the receiver member 804 about the axis A2. The shank 802 can also be rotatable relative to the receiver member 804 about any of a plurality of other axes, e.g., one or more axes perpendicular to the axis A1 such as an axis A3 as shown.

A bushing 830 can be disposed between the head 810 of the shank 802 and the distal seat of the receiver member 804 to supply a first drag force. The bushing 830 can include a split to allow for radial expansion and compression of the bushing. While a split bushing is shown, the bushing 830 can include other features for allowing radial expansion and compression, such as slits, cut-outs, and the like. The exterior surface of the bushing 830 can be configured for polyaxial movement within the seat of the receiver member 804, e.g., such that the bushing can rotate about the axis A3 relative to the receiver member or about various other axes. For example, the bushing 830 can include a spherical exterior surface that engages a corresponding spherical interior surface of the receiver member 804. The interior surface of the bushing 830 can have a geometry configured to exert a drag force on the head 810 of the shank 802. For example, at least a portion of the interior surface of the bushing 830 can define a spherical surface having a resting diameter that is less than the diameter of the head 810 of the shank 802. Accordingly, once assembled to the shank 802, the bushing 830 can exert a frictional drag force against the head 810 of the shank, resisting polyaxial motion between the head of the shank and the bushing, e.g., about the axis A3. The bushing 830 can include an over-rotation blocking feature. For example, the bushing 830 can include a proximal lip or shoulder (not shown) configured to contact a stop feature of the bone anchor 800 to prevent over-rotation of the bushing. The lip can have an outer diameter that is greater than an outer diameter of a distal portion of the bushing. In some embodiments, the lip can be formed by a groove formed in the exterior surface of the bushing 830.

The distal seat formed in the receiver member 804 can act as the stop feature that is contacted by the proximal lip of the bushing 830 to prevent over-rotation of the bushing. In particular, as the bushing 830 rotates relative to the receiver member 804, e.g., about the axis A3, to a rotation limit, the lip can contact the distal seat to prevent further rotation of the bushing relative to the receiver member.

The saddle 818 can be biased to expand longitudinally along the axis A1 to supply a second drag force. The saddle 818 can include a proximal component 818P, a distal component 818D, and a wave spring or other bias element 850 disposed between the proximal and distal components to urge the components away from each other along the axis A1. The proximal component 818P can include opposed arms 820A, 820B configured to receive a spinal rod or other fixation element therebetween. The distal component 818D can include a bearing surface configured to contact the bushing 830 (or the head 810) to exert a drag force and, when the closure mechanism 808 is tightened, to lock polyaxial movement between the receiver member 804 and the shank 802.

When installed in the receiver member 804, distal travel of the saddle 818 can be limited by contact with the bushing 830 or, in embodiments in which the bushing is omitted, with the head 810 of the shank 802. Also when installed in the receiver member 804, proximal travel of the saddle 818 can be limited by contact with a ledge or shoulder of the receiver member, e.g., defined by one or more protrusions 834 that extend radially-inward from the inner sidewall of the receiver member. The longitudinal spacing between the protrusions 834 and the bushing 830 (or the head 810) can be less than the resting longitudinal dimension of the saddle 818. Accordingly, when disposed between the protrusions 834 and the bushing 830 (or the head 810), the wave spring or other bias element 850 is compressed from its resting state. Resilient material properties of the bias element 850 can thereby cause the saddle to exert a distal biasing force against the bushing 830 (or the head 810) substantially along the axis A1. The saddle 818 can thus supply a second drag force, resisting polyaxial motion between the bushing 830 and the receiver member 804, e.g., rotation about the axis A3.

It will be appreciated that the relative dimensions of the bone anchor 800 components can be selected to achieve the desired drag forces, and/or to achieve the desired relative drag applied by the first drag force and the second drag force. In some embodiments, the first and second drag forces can be selected to be different, e.g., such that the shank 802 initially moves relative to the bushing 830 and only after the shank reaches maximum angulation relative to the bushing does the bushing move relative to the receiver member 804. Such an arrangement can advantageously reduce the risk of over-rotation of the bushing 830 relative to the receiver member 804, e.g., about the axis A3, which could undesirably weaken the construct. The bone anchor 800 can include additional or alternative over-rotation blocking features, including those described herein.

Figure 8A:
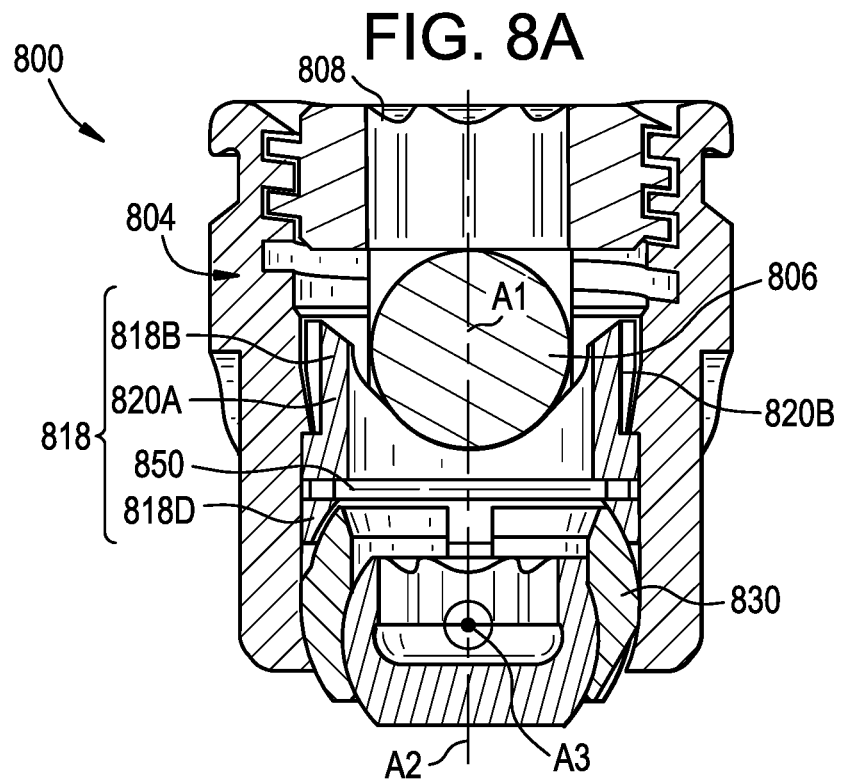
FIG. 8A is a sectional side view of a bone anchor and a spinal rod.
Figure 8B:
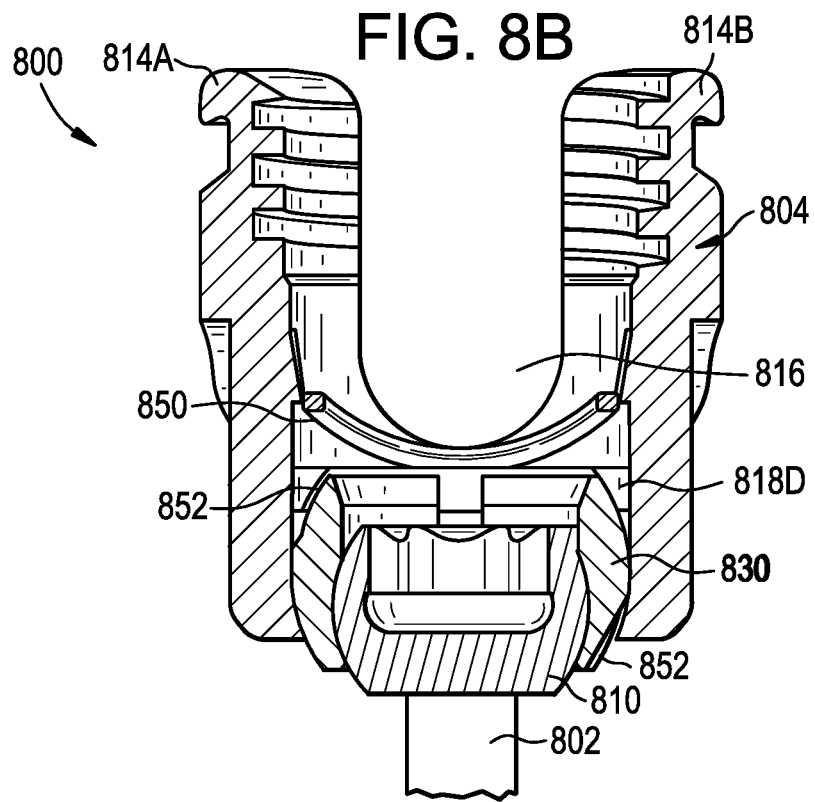
FIG. 8B is a partially exploded sectional side view of the bone anchor of FIG. 8A.
Figure 8C:
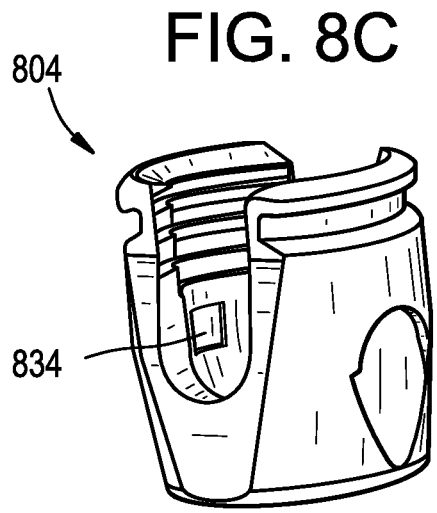
FIG. 8C is a perspective view of a receiver member of the bone anchor of FIG. 8A.
Figure 8D:
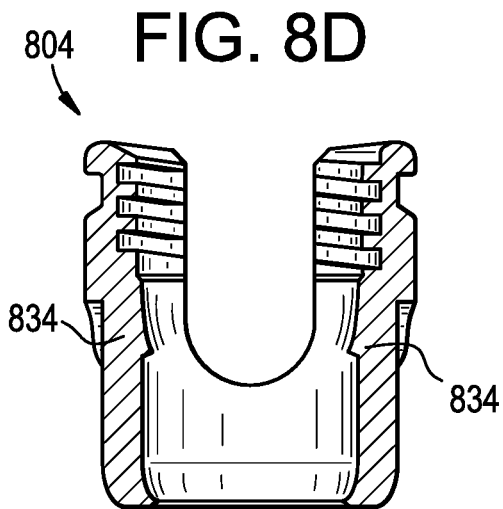
FIG. 8D is a sectional side view of the receiver member of FIG. 8C.
Figure 8E:
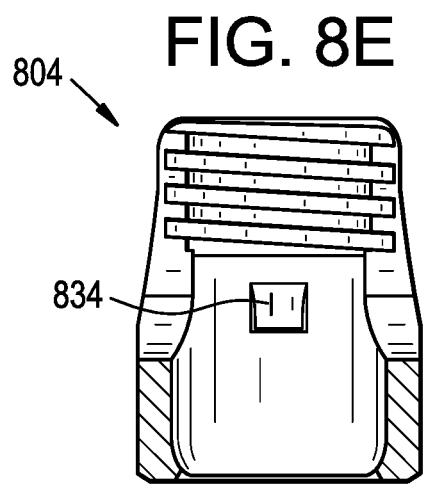
FIG. 8E is another sectional side view of the receiver member of FIG. 8C.
Figure 8F:
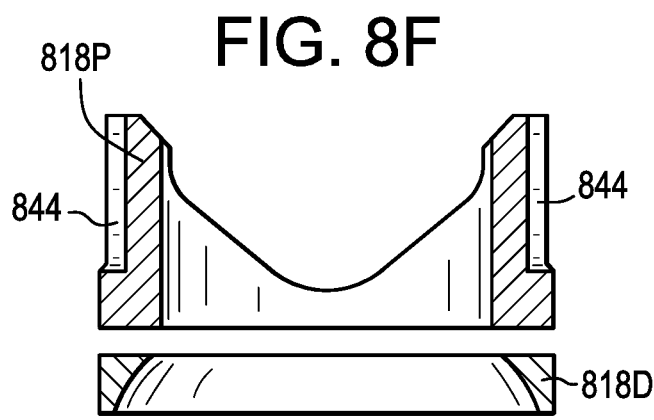
FIG. 8F is a sectional side view of a saddle of the bone anchor of FIG. 8A.
Figure 8G:
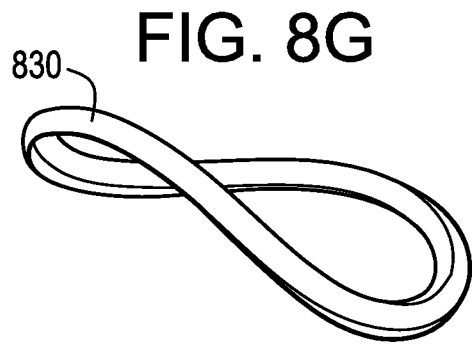
FIG. 8G is a perspective view of a bias element of the bone anchor of FIG. 8A.
Figure 8H:
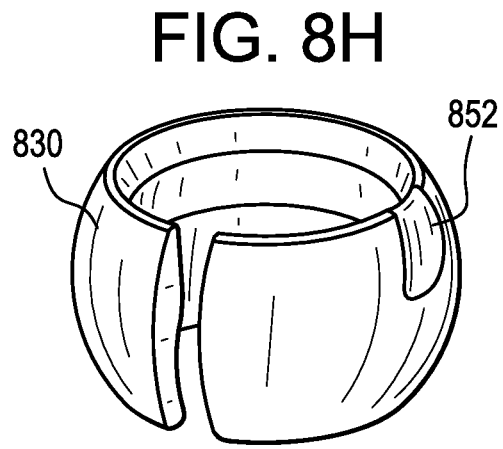
FIG. 8H is a perspective view of a bushing of the bone anchor of FIG. 8A.

In some embodiments, the saddle 818 can include anti-rotation features to limit or prevent rotation of the saddle relative to the receiver member 804 about the axis A1. For example, each arm 820A, 820B of the saddle 818 can include a keyway 844 in which a protrusion 834 of the receiver member 804 is received to limit or prevent rotation of the saddle 818 relative to the receiver member about the axis A1. This engagement between the protrusions 834 and the keyways 844 can also be effective to retain the saddle 818 within the receiver member 804. The bushing 830 can include one or more reliefs 852 to allow the bushing to be inserted distally past the protrusions 834 of the receiver member 804 during assembly. For example, as shown in FIG. 8B, the bushing 830 can include a first relief 852 formed at a proximal end of the bushing and a second relief formed on an opposite side of the bushing at a distal end of the bushing. The illustrated reliefs 852 can allow the bushing to be inserted past the protrusions 834, e.g., by rotating the bushing 830 such that a central longitudinal axis of the bushing is obliquely angled with respect to the axis A1 and such that the reliefs 852 are aligned with the protrusions 834.

In use, the shank 802 of the bone anchor 800 can be driven into bone using known techniques. The receiver member 804 can then be rotated relative to the shank 802 to an initial position as desired by the user, e.g., to provisionally position the receiver member to receive a spinal rod 806. The first and/or second drag forces can maintain the receiver member 804 in this initial position prior to locking the construct, preventing the receiver member from "flopping" over. The first and second drag forces can thus prevent unintended movement prior to locking the bone anchor 800, while still allowing free movement when intended by the user. Eventually, the closure mechanism 808 can be applied to the bone anchor 800 to lock the assembly and/or to secure a spinal rod 806 within the receiver member 804.

Figure 9A:
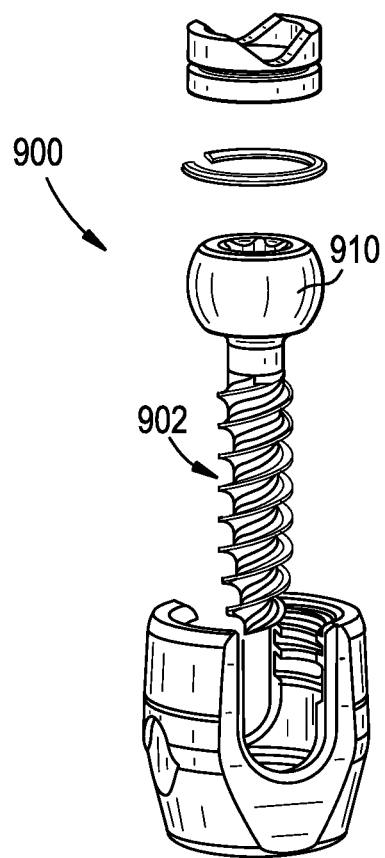
FIG. 9A is an exploded perspective view of a bone anchor.
Figure 9B:
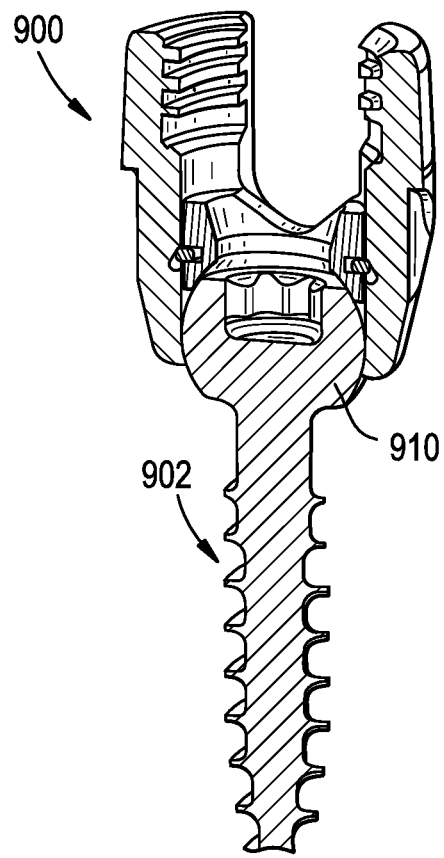
FIG. 9B is a sectional perspective view of the bone anchor of FIG. 9A.

FIGS. 9A-9B illustrate a bone anchor 900 that is identical to the bone anchor 500 described above, except that the bushing is omitted from the bone anchor 900. In embodiments in which the bushing is omitted, the head 910 of the shank 902 can be enlarged to occupy the space within the receiver member that would otherwise be occupied by a bushing. While a version of the bone anchor 500 that omits the bushing is shown in FIGS. 9A-9B, it will be appreciated that the bushing can be omitted from any of the other bone anchors disclosed herein, e.g., the bone anchors 200, 300, 400, 600, 700, 800.

Figure 10:
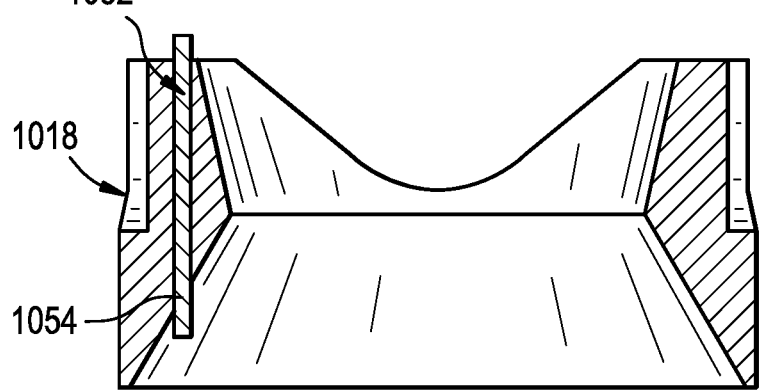
FIG. 10 is a sectional side view of a saddle.

Any of the bone anchors disclosed herein can include alternative or additional features for supplying drag force. For example, as shown in FIG. 10, in some embodiments, the saddle 1018 can include a protrusion 1054 that extends distally therefrom to drag on the bushing (or the head in embodiments in which the bushing is omitted). The protrusion 1054 can be formed by drilling a hole in the saddle and inserting a rod or pin 1052 through the hole such that the rod sits proud of the distal surface of the saddle 1018. The protruding portion 1054 of the rod 1052 can drag against the bushing or the head of the shank to apply a drag force thereto prior to locking the bone anchor. The rod 1052 can be formed from a compressible material such as PEEK or other polymers, such that the rod compresses out of the way so as not to interfere with locking when the closure mechanism is tightened to the receiver member.

In embodiments that include a drag ring or clip, the geometry of the drag ring can be selected to achieve the desired or optimal drag force. For example, increasing the height of the drag ring along the longitudinal or proximal-distal axis of the receiver member can advantageously provide a smoother drag action and reduce skipping and catching that may occur with drag rings having a smaller height. Also, increasing the height and reducing the width of the drag ring can allow for corresponding changes in the groove formed in the receiver member. A taller, shallower groove may weaken the structure of the receiver member less than a shorter, deeper groove.

In some embodiments, the drag ring has a height dimension parallel to the central longitudinal axis of the receiver member, the height dimension extending from a proximal surface of the drag ring to a distal surface of the drag ring, and a width dimension perpendicular to the height dimension, the width dimension extending from an inner surface of the drag ring to an outer surface of the drag ring. A ratio of the height dimension to the width dimension can be at least 2:1. A ratio of the height dimension to the width dimension can be at least 3:1. A ratio of the height dimension to the width dimension can be at least 4:1. Referring again to FIGS. 4A-4B, an embodiment is shown in which the ring 432 has a height-to-width aspect ratio (H:W) of about 3.5:1.

Any of the bone anchors disclosed herein can include a drag feature, an over-rotation blocking feature, or both. Any of the bone anchors disclosed herein can omit the disclosed drag feature and include the disclosed over-rotation blocking feature. Any of the bone anchors disclosed herein can include the disclosed drag feature and omit the disclosed over-rotation blocking feature. Various other combinations of the disclosed features can be included or omitted, as will be readily appreciated by one having ordinary skill in the art in view of the present disclosure.

An exemplary method of using the bone anchors disclosed herein is described below. While the exemplary method is described with respect to the bone anchor 200, it will be appreciated that the other bone anchors disclosed herein can be used in the same or in a similar manner. The bone anchor 200 can be provided for a surgery in a state of partial disassembly or can be preassembled.

The bone anchor 200 can be delivered to a target bone site within the patient and driven to a desired depth along a desired trajectory using known techniques. Prior to attaching and/or tightening the closure mechanism 208 to the bone anchor 200, the receiver member 204 can be positioned in a desired orientation relative to the shank 202. For example, the receiver member 204 can be polyaxially rotated about the bushing 230, and/or the bushing 230 can be polyaxially rotated about the head 210 of the shank 202. Prior to attaching and/or tightening the closure mechanism 208 to the bone anchor 200, the receiver member 204 can be maintained in the desired orientation, e.g., via a drag force between the ring 232 and the bushing 230 and/or via a drag force between the bushing and the head 210.

Figure 2A:
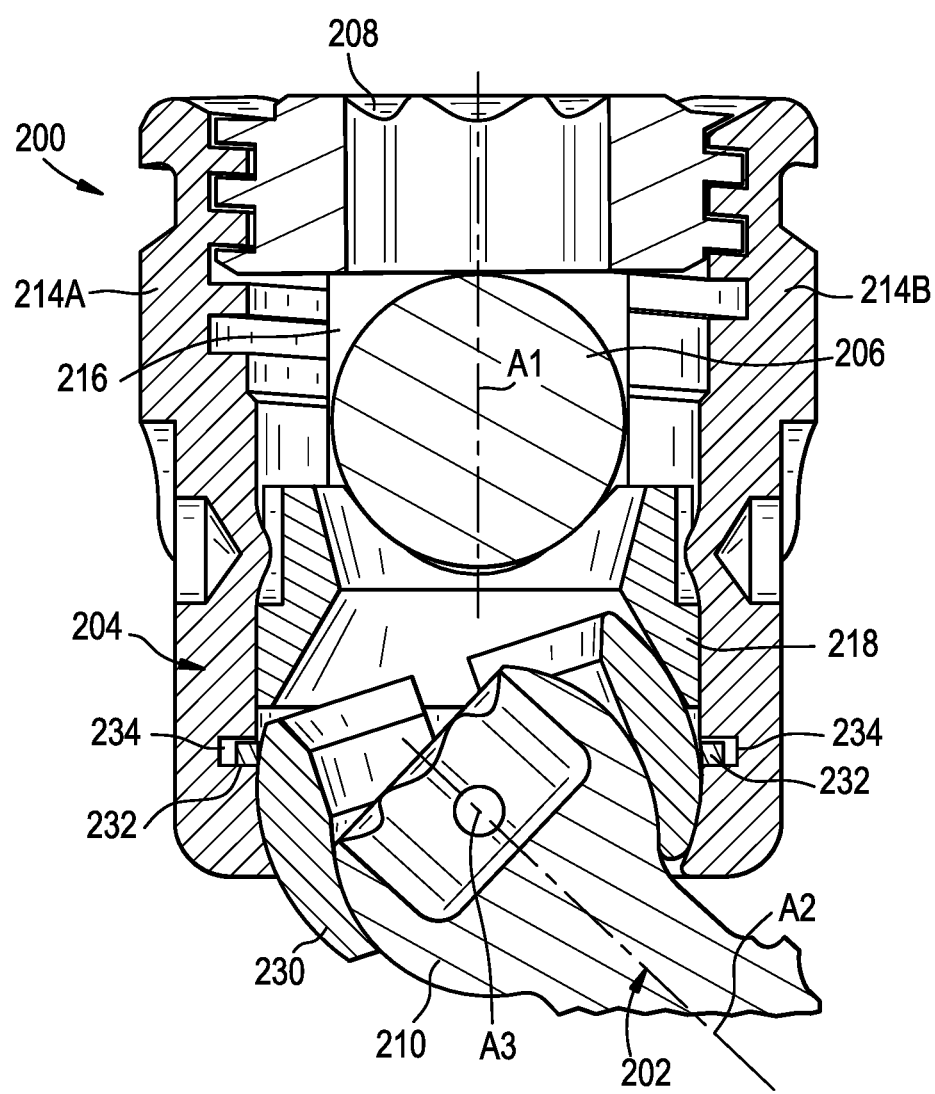
FIG. 2A is a sectional side view of a bone anchor and a spinal rod.

The bone anchor 200 can be used to secure an implant to the bone. For example, as shown in FIG. 2A, a spinal rod 206 can be inserted into the rod-receiving recess 216 of the receiver member 200. Before the rod 206 is fully seated and locked within the receiver member 204, the shank 202 can remain movable relative to the receiver member, with the drag force(s) resisting unintended movement while allowing free movement when specifically intended by the user, e.g., by applying an input force sufficient to overcome the drag force. The set screw or other closure mechanism 208 can be applied to the receiver member 204 to urge the rod 206 and the saddle 218 distally with respect to the receiver member and thereby lock the bone anchor 200. In particular, applying the closure mechanism 208 can be effective to lock movement of the receiver member 204 relative to the shank 202. Applying the closure mechanism 208 can also be effective to lock movement of the rod 206 relative to the receiver member 204. As noted above, a dual set screw or other construct can be used to independently lock movement of the shank 202 relative to the receiver member 204 and movement of the rod 206 relative to the receiver member.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the devices and methods illustrated and described herein generally involve attaching spinal rods to vertebrae, it will be appreciated that the devices and methods herein can be used with various other types of fixation or stabilization hardware, in any bone, in non-bone tissue, or in non-living or non-tissue objects. The bone anchors and other implants disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, cobalt-chromium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:
1. A bone anchor, comprising:
   a receiver member that defines a cavity and a rod-receiving recess, the receiver member having proximal and distal ends and a central longitudinal axis;
   a bushing disposed in the cavity;
   a shank having a head portion retained within the bushing and a bone engaging portion that protrudes distally from the receiver member; and
   a drag ring that applies a frictional force to the bushing, the drag ring being disposed in a groove formed in the receiver member,
   wherein the bushing includes a split configured to allow for radial expansion and compression of the bushing, and
   wherein a distal opening of the cavity of the receiver member has a diameter that is less than a maximum diameter of the bushing,
   wherein, with the drag ring disposed in the groove, the drag ring is configured to contact the bushing at a point along an outer surface of the bushing at a maximum diameter of the bushing.

2. The bone anchor of claim 1, wherein the head portion of the shank is rotatable with respect to the bushing and wherein the bushing exerts a frictional force on the head of the shank.

3. The bone anchor of claim 1, further comprising a fastener configured to be applied to the receiver member to (i) prevent rotation of the head portion of the shank relative to the bushing and (ii) prevent rotation of the bushing relative to the receiver member.

4. The bone anchor of claim 1, wherein the bushing includes an over-rotation blocking feature.

5. The bone anchor of claim 4, wherein the blocking feature comprises a lip formed at a proximal end of the bushing, the lip being configured to contact the drag ring to limit rotation of the bushing relative to the receiver member.

6. The bone anchor of claim 5, wherein the drag ring has a ramped distal-facing surface oriented at an oblique angle to the central longitudinal axis of the receiver member.

7. The bone anchor of claim 6, wherein the drag ring has a planar proximal-facing surface oriented perpendicular to the central longitudinal axis of the receiver member.

8. The bone anchor of claim 4, wherein the blocking feature comprises a lip formed at a proximal end of the bushing, the lip being configured to contact the groove of the receiver member to limit rotation of the bushing relative to the receiver member.

9. The bone anchor of claim 1, further comprising a saddle disposed in the cavity proximal to the bushing, wherein the saddle includes a distal-facing surface with a drag pin extending distally therefrom.

10. The bone anchor of claim 1, wherein an interior surface of the bushing is configured to exert a frictional drag force against the head of the shank.

11. The bone anchor of claim 1, wherein the bushing is configured for polyaxial movement within the cavity of the receiver member.

12. A bone anchor, comprising:
a receiver member that defines a cavity and a rod-receiving recess, the receiver member having proximal and distal ends and a central longitudinal axis;
a bushing disposed in the cavity;
a shank having a head portion retained within the bushing and a bone engaging portion that protrudes distally from the receiver member; and
a drag ring disposed in a groove formed in the receiver member that exerts a frictional force against the bushing to resist polyaxial movement between the bushing and the receiver member,
wherein, with the drag ring disposed within the groove, the drag ring applies the frictional force radially to an outer surface of the bushing.

13. The bone anchor of claim 12, wherein at least a portion of the interior surface of the drag ring has a resting diameter that is less than an external diameter of the bushing.

14. The bone anchor of claim 12, wherein the drag ring includes one or more teeth that extend radially-inward from a circular main body of the drag ring.

15. The bone anchor of claim 12, further comprising a saddle positioned within the receiver member.

16. The bone anchor of claim 15, wherein the drag ring is disposed between the bushing and the saddle.

17. The bone anchor of claim 12, wherein, with the drag ring disposed in the groove, the drag ring is configured to contact the bushing at a point along the outer surface of the bushing at a maximum diameter of the bushing.

18. The bone anchor of claim 12, wherein, with the drag ring disposed in the groove, the drag ring applies the frictional force to a convex outer surface of the bushing.

19. The bone anchor of claim 12, wherein an interior surface of the bushing includes a spherical surface having a resting diameter that is less than a diameter of the head portion of the shank.

20. A bone anchor, comprising:
a receiver member that defines a cavity and a rod-receiving recess, the receiver member having proximal and distal ends and a central longitudinal axis;
a bushing disposed in the cavity;
a shank having a head portion retained within the bushing and a bone engaging portion that protrudes distally from the receiver member; and
a drag ring disposed in a groove formed in the receiver member that exerts a frictional force against the bushing to resist polyaxial movement between the bushing and the receiver member,
wherein the drag ring includes one or more teeth that extend radially-inward from a circular main body of the drag ring.

21. A bone anchor, comprising:
a receiver member that defines a cavity and a rod-receiving recess, the receiver member having proximal and distal ends and a central longitudinal axis;
a bushing disposed in the cavity;
a shank having a head portion retained within the bushing and a bone engaging portion that protrudes distally from the receiver member; and
a drag ring disposed in a groove formed in the receiver member that exerts a frictional force against the bushing to resist polyaxial movement between the bushing and the receiver member,
wherein, with the drag ring disposed in the groove, the drag ring applies the frictional force to a convex outer surface of the bushing.

* * * * *